United States Patent
Ding et al.

(10) Patent No.: US 7,405,220 B2
(45) Date of Patent: Jul. 29, 2008

(54) PYRAZOLOPYRIMIDINES

(75) Inventors: Qingjie Ding, Bridgewater, NJ (US);
Nan Jiang, Fairfield, NJ (US); John Lawson Roberts, Budd Lake, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 386 days.

(21) Appl. No.: 11/136,023

(22) Filed: May 24, 2005

(65) Prior Publication Data

US 2005/0277655 A1 Dec. 15, 2005

Related U.S. Application Data

(60) Provisional application No. 60/578,235, filed on Jun. 9, 2004.

(51) Int. Cl.
*C07D 239/70* (2006.01)
*A61K 31/4162* (2006.01)

(52) U.S. Cl. .................. 514/262.1; 544/262

(58) Field of Classification Search ............ 544/262; 514/262.1
See application file for complete search history.

(56) References Cited

U.S. PATENT DOCUMENTS

| | | | |
|---|---|---|---|
| 5,654,307 A | 8/1997 | Bridges et al. | |
| 6,107,305 A | 8/2000 | Misra et al. | |
| 2002/0198171 A1 | 12/2002 | Schinazi et al. | |
| 2005/0203091 A1* | 9/2005 | Arora et al. | 514/234.5 |

FOREIGN PATENT DOCUMENTS

| WO | WO 91/18887 | 12/1991 |
|---|---|---|
| WO | WO 99/21845 | 5/1999 |
| WO | WO 00/12485 | 3/2000 |
| WO | WO 00/39101 | 7/2000 |
| WO | WO 01/19825 | 3/2001 |
| WO | WO 01/38315 | 5/2001 |
| WO | WO 01/79198 | 5/2001 |
| WO | WO 01/64653 | 9/2001 |
| WO | WO 01/64654 | 9/2001 |
| WO | WO 01/64656 | 9/2001 |
| WO | WO 02/057261 | 7/2002 |
| WO | WO 02/090360 A1 | 11/2002 |
| WO | WO 03/097048 | 11/2003 |
| WO | WO 2004/069139 | 8/2004 |
| WO | WO 2004/087707 A1 | 10/2004 |

OTHER PUBLICATIONS

Kim et al. KR 2004026462, CAS abstract, Mar. 31, 2004.*
Carlson et. al., *Cancer Res.*. 1996, 56, 2973-2978.
De Azevedo et al., *Eur. J. Biochem.*, 1997, 243, 518-526.
Bridges, A.J., *Exp. Opin. Ther. Patents*. 1995, 5, 12451257.
Orr et al., *J. Biol. Chem.* 1998, 273, 3803-3807.
Kakeya, H. et. al., *Cancer Res.*. 1998, 58, 704-710.
Harper, J.W., *Cancer Surveys* 1997, 29, 91-107.
Harrington, E.A., et al., *Proc. Natl. Acad. Sci. USA* 1998, 95, 11945-11950.
Leostim, et al., *Eur. J. Biochem.(FEBS)* 2000, 267, 5983-5994.
Garrett, M.D. et. al., *Current Opin. Genetics Develop.* 1999, 9, 104-111.
McBonyebi, O. P. et al., *Cancer Res.*. 1999, 59, 1903-1910.
Hoessel et al., *Nature Cell Biology*. 1999, 1, 60-67.
Zaherevitz et al., *Cancer Res.*, 1999, 59, 2566-2569.
Sielecki, T.M., et al., *Bioorg. Med. Chem. Lett.* 2001, 11, 1157-1160.
Nugiel, D. A., et al., *J. Med. Chem.*, 2001, 44, 1334-1336.
Fry, D. W. et al., *J. Biol. Chem.* 2001, 276, 16617-16623.
Soni, R., et al., *Biochem. Biophys. Res. Commun.* 2000, 275, 877-884.
Ryu, C-K. et al., *Bioorg. Med. Chem. Lett.*, 2000, 10, 461-464.
Jeong, H-W., et al., *Bioorg. Med. Chem. Lett.*. 2000, 10, 1819-1822.
Barvian et al., *J. Med. Chem.*, 2000, 43, 4606-4616.
Chong, W., Fischer, *Curr. Opin. in Drug Discov. and Develop.*, 2001, 4, 623-634.
Harris, W. and Wilkinson, S., *Emerging Drugs*. 2000, 5, 287-297.
Dumas, J., *Exp. Opin. Ther. Patents*. 2001, 11, 405-429.
Sielecki T., et. al., *J. Med. Chem.*. 2000, 43, 1-18.

* cited by examiner

*Primary Examiner*—Bruck Kifle
(74) *Attorney, Agent, or Firm*—George W. Johnston; Patricia S. Rocha-Tramaloni

(57) ABSTRACT

Novel pyrazolopyrimidines of formula (I):

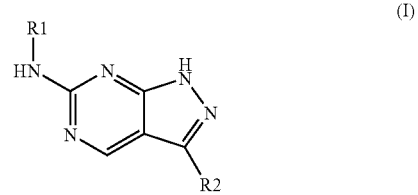

are discussed. These pyrazolopyrimidines are capable of inhibiting the activity of cyclin-dependent kinases, most particularly cyclin-dependent kinase 1 (Cdk1), cyclin-dependent kinase 2 (Cdk2), and cyclin-dependent kinase 4 (Cdk4) and are thus useful, inter alia, in the treatment or control of cancer, in particular solid tumors. This invention also provides pharmaceutical compositions containing such compounds and to methods of treating or controlling cancer, most particularly the treatment or control of breast, lung, colon and prostate tumors.

13 Claims, No Drawings

PYRAZOLOPYRIMIDINES

PRIORITY TO RELATED APPLICATIONS

This application claims the benefit of Provisional Application Ser. No. 60/578,253, filed Jun. 9, 2004.

FIELD OF THE INVENTION

The present invention provides novel pyrazolopyrimidines of formula (I):

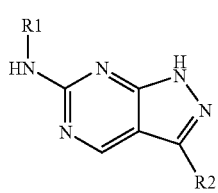

The novel pyrazolopyrimidines are capable of inhibiting the activity of cyclin-dependent kinases, most particularly cyclin-dependent kinase 1 (Cdk1), cyclin-dependent kinase 2 (Cdk2), and cyclin-dependent kinase 4 (Cdk4). These compounds and their pharmaceutically acceptable salts and esters have antiproliferative activity and are useful, inter alia, in the treatment or control of cancer, in particular solid tumors. This invention also provides pharmaceutical compositions containing such compounds and to methods of treating or controlling cancer, most particularly the treatment or control of breast, lung, colon and prostate tumors.

BACKGROUND OF THE INVENTION

Uncontrolled cell proliferation is the hallmark of cancer. Cancerous tumor cells typically have some form of damage to the genes that directly or indirectly regulate the cell-division cycle.

The progression of cells through the various phases of the cell cycle is regulated by a series of multienzyme complexes consisting of a regulatory protein, a cyclin, and a kinase. These kinases are called cyclin-dependent kinases (Cdks). The Cdks are expressed throughout the cell cycle, while the levels of the cyclins vary depending on the stage of the cell cycle.

The four primary phases of cell cycle control are generally describes as $G_1$, S, $G_2$, and M. Some essential enzymes for cell cycle control appear to be cyclin D/Cdk4, cyclin D/Cdk6, cyclin E/Cdk2, cyclin A/Cdk2, and cyclin B/Cdk1 (also known as Cdc2/cyclin B). Cyclin D/Cdk4, cyclin D/Cdk6, and cyclin E/Cdk2 control passage through the $G_1$-phase and the $G_1$- to S-phase transition by phosphorylation of the retinoblastoma phosphoprotein, pRb. Cyclin A/Cdk2 regulates passage through the S-phase, and cyclin B/Cdk1 controls the $G_2$ checkpoint and regulates entry into M (mitosis) phase.

The cell cycle progression is regulated by Cdk1 (cdc2) and Cdk2 beyond early $G_1$ when cells are committed to cytokinesis. Therefore, drug inhibition of these Cdks is likely not only to arrest cell proliferation, but also to trigger apoptotic cell death. Once the cells pass the $G_1$ restriction point and are committed to S phase, they become independent of growth factor stimulation for continued cell cycle progression.

Following completion of DNA replication, cells enter the $G_2$ phase of the cell cycle in preparation for M phase and cytokinesis. Cdk1 has been shown to regulate passage of cells through these later phases of the cell cycle in association with both cyclins A and B. Complete activation of Cdk1 requires both cyclin binding and specific phosphorylation (Morgan, D. O., De Bondt, H. L., Curr. Opin. Cell. Biol. 1994, 6, 239-246). Once activated, Cdk1/cyclin complexes prepare the cell for division during M phase.

The transition from $G_1$ phase into S phase as stated above is regulated by the complex of Cdk4 with cyclin D and Cdk2.with cyclin E. These complexes phosphorylate the tumor suppressor protein Retinoblastoma (pRb), releasing the transcription factor E2F and allowing the expression of genes required in S phase (Nevins, J. R. Science 1992, 258, 424-429; Lavia, P. BioEssays 1999, 21, 221-230). Blocking the activity of the Cdk4/cyclin D and Cdk2/cyclin E complexes arrests the cell cycle in $G_1$ phase. For example, the proteins of the INK4 family, including $p16^{INK4a}$, which block the kinase activity of the Cdk4/cyclin D complex, cause arrest in $G_1$ (Sherr, C. J. Science 1996, 274, 1672-1677). The specific block has been reviewed (Vidal, A. Gene 2000, 247, 1-15).

Recent experiments show that the complex of Cdk4 with cyclin D3 also plays a role in cell cycle progression through $G_2$ phase. Inhibition of this complex, either by p16 or using a dominant negative Cdk4, results in arrest in $G_2$ phase in cells that do not express pRb (Gabrielli B. G. et al. J. Biol. Chem. 1999, 274, 13961-13969).

Numerous defects in the pRb pathway have been shown to be involved in various cancers. For example, overexpression of Cdk4 has been observed in cases of hereditary melanoma (Webster, K. R. Exp. Opin. Invest. Drugs 1998, 7, 865-887); cyclin D is overexpressed in many human cancers (Sherr, C. J. Science 1996, 274, 1672-1677); p16 is mutated or deleted in many tumors (Webster, K. R. Exp. Opin. Invest. Drugs 1998, 7, 865-887); and pRb function is lost through mutation or deletion in many human cancers (Weinberg, R. A. Cell 1995, 81, 323-330). Defects in this pathway have also been shown to have an effect on prognosis. For example, loss of p16 is correlated with poor prognosis in non-small-cell lung carcinoma (NSCLC) and malignant melanoma (Tsihlias, J. et al. Annu. Rev. Med. 1999, 50, 401-423). Abnormalities of cyclin D1 and/or pRb at the gene and/or expression level were present in more than 90% of a series of non-small cell lung cancer specimens, indicating that cyclin D1 and/or pRb represent an important step in lung tumorigenesis (Marchetti, A. et. al. Int. J. Cancer 1998, 75, 573-582). In 49 out of 50 pancreatic carcinomas (98%), the pRb/p16 pathway as abrogated exclusively through inactivation of the p16 gene and cyclin D connected (schutte, M. et. al. Cancer Res. 1998, 57, 3126-3134). For a review on the relation between expression of pRb and the cyclin/cyclin dependent kinases in a number of tissues, see Teicher, B. A. Cancer Chemother. Pharmacol. 2000, 46, 293-304.

Because of the involvement of the Cdk4/cyclin D/pRb pathway in human cancer through its role in regulating progression of the cell cycle from $G_1$ to S phase, and the potential therapeutic benefit from modulating this pathway, there has been considerable interest in agents that inhibit or promote elements of this pathway. For example, effects on cancer cells have been shown using antibodies, antisense oligonucleotides and overexpression or addition of protiens involved in the pathway. See, e.g., Lukas, J. et al. *Nature* 1995, 79, 573-582; Nevins, J. R. *Science* 1992, 258, 424-429; Lim, I. K. et al. *Molecular Carcinogenesis* 1998, 23, 25-35; Tam, S. W. et al. *Oncogene* 1994, 9, 2663-2674; Driscoll, B. et al. *Am. J. Physiol.* 1997, 273 (*Lung Cell. Mol. Physiol.*), L941-L949; and Sang, J. et al. *Chin. Sci. Bull.* 1999, 44, 541-544).

The role of cdks in the regulation of cellular proliferation is thus well established. For example, as shown above, there is an extensive body of literature validating the use of compounds inhibiting targets in the Cdk4, Cdk2 and Cdk1 pathways as anti-proliferative therapeutic agents. Inhibitors of cellular proliferation thus act as reversible cytostatic agents that are useful in the treatment of disease processes which feature abnormal cellular growth, such as cancers and other cell proliferative disorders including, for example inflammation (e.g. benign prostate hyperplasia, familial adenomauosis, polyposis, neuro-fibromatosis, atherscelorsis, pulmonary fibrosis, arthritis, psoriasis, inflammatory bowel disease, transplantation rejection infections), viral infections (including, but not limited to herpervirus, poxvirus, Epstein-Barr virus), autoimmune disease (e.g. lupus, theumatoid arthritis, psoriasis, inflammatory bowel disease), neurodegenerative disorders (including but not limited to Alzheimer's disease), an neurodegenerative diseases (e.g. Parkinson's disease, amyotriphic lateral scelorsis, retinitis pigmentosa, spinal muscular atrophy, and cerebral degeneration).

Several distinct classes of small molecules have been identified as inhibitors of Cdks: olomoucine and other purine analogs, flavopiridol, staurosporine, UCH-01 and other indolocarbazoles, 9-hydroxyellipticine, indirubin, paullones, diary ureas, quinazolines, indopyrazoles, [2,3-d]pyridopyrimidines, fascaplysin, aminothiazoles, diaminothiazoles, pteridinones, and pyrazoles or example (Carlson et. al., *Cancer Res.* 1996, 56, 2973-2978: De Azevedo et al., *Eur. J. Biochem.*, 1997, 243, 518-526; Bridges, A. J., *Exp. Opin. Ther. Patents.* 1995, 5, 12451257; Reinhold et al., *J. Biol. Chem.* 1998, 278, 3803-3807; Kakeya, H. et al., *Cancer Res.* 1998, 58, 704-710; Harper, J. W., *Cancer Surveys* 1997, 29, 91-107; Harrington, E. A., et al., *Proc. Natl. Acad. Sci. USA* 1998, 95, 11945-11950; Meijer, L., et al., *Eur. J. Biochem.* 2000, 267, 1-13; Garrett, M. D. et. al., *Current Opin. Genetics Develop.* 1999, 9, 104-111; Mgbonyebi, O. P. et al., *Cancer Res.* 1999, 59, 1903-1910; Hoessel et al., *Nature Cell Biology.* 1999, 1, 60-67; Zaherevitz et al., *Cancer Res.*, 1999, 59, 2566-2569; Honma, T., et al., 221$^{St}$ *National ACS Meeting.* 2001: Medi 136; Sielecki, T. M., et al., *Bioorg. Med. Chem. Lett.* 2001, 11, 1157-1160: Nugiel, D. A., et al., *J. Med. Chem.*, 2001, 44, 1334-1336; Fry, D. W. et al., *J. Biol. Chem.* 2001, 276, 16617-15523; Soni, R., et al., *Biochem. Biophys. Res. Commun.* 2000, 275, 877; Ryu, C-K. et al., *Bioorg. Med. Chem. Lett.*, 2000, 10, 461; Jeong, H-W., et al., *Bioorg. Med. Chem. Lett.* 2000, 10, 1819; Toogood et al., *J. Med. Chem.*, 2000, 43, 4606-4616; Chong, W., Fischer, *Curr. Opin. in Drug Discov. and Develop.*, 2001, 4, 623-634, WO0009921845, Toogood. P., WO0119825, Toogood P., WO0238315, Reich S. H., WO0179198, Webster, K. U.S. Pat. No. 6,262,096.

The class of diaminopyridimines is represented by compounds of formula

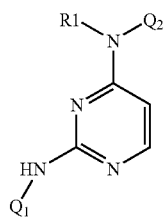

stated to inhibit Cdk4 and FAK3. See WO0012485 (Astra Zeneca).

WO9118887 (Smith Kline Beecham) related to diaminopyrimidines of formula

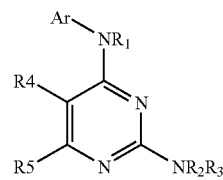

that are stated to inhibit gastric secretion.

WO0039101 (Astra Zeneca) related to pyrimidine compounds of formula

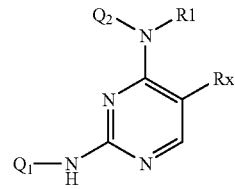

stated to act as anti-cancer agents.

WO0164653 (Astra Zeneca) relates to pyrimidine compounds of the formula

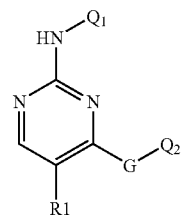

described to act as Cdk inhibitors and FAK inhibitors.

WO0164654 (Astra Zeneca) relates to pyrimidine compounds of formula

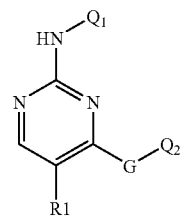

described to act as Cdk inhibitors and FAK inhibitors.

Additionally, WO0164656 (Astra Zeneca) relates to pyrimidine compounds of formula

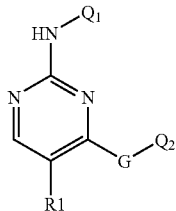

also described as Cdk inhibitors and FAK inhibitors.

For reviews of compounds inhibiting the Cdk4/cyclin D pathway see: Harris, W. and Wilkinson, S., *Emerging Drugs.* 2000, 5, 287-297; Dumas, J., *Exp. Opin. Ther. Patents.* 2001, 11, 405-429; Sielecki T., et. al., *J. Med. Chem.* 2000, 43, 1-18.

SUMMARY OF THE INVENTION

The present invention provides novel pyrazolopyrimidines having the formula (I):

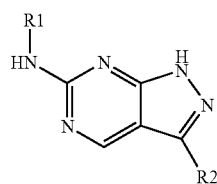

or the pharmaceutically acceptable salts or esters thereof, wherein
$R^1$ is selected from the group consisting of:
(a) heterocycle which may be substituted by up to four substituents independently selected from the group consisting of:
  (i) lower alkyl which may be substituted by OH, $CO_2R^3$, $COR^4$, $CONR^5R^6$, $NR^5R^6$, $OR^7$, or $S(O)nR^8$; and
  (ii) $CO_2R^3$, $COR^4$, $CONR^5R^6$, $NR^5R^6$, $OR^7$ or $S(O)nR^8$;
(b) aryl which may be substituted by up to four substituents independently selected from the group consisting of:
  (i) $S(O)nR^8$, $NR^5R^6$, lower alkyl, $OR^7$, halogen or lower alkyl which may be substituted by OH, $CO_2R^3$, $COR^4$, $CONR^5R^6$, $NR^5R^6$ or $OR^7$;
  (ii) COOH; and
carbonyl substituted by lower alkyl, $OR^7$, or $NR^5R^6$;
(c) cycloalkyl which may be substituted by $OR^7$, $NR^5R^6$, or $S(O)nR^8$; and
(d) lower alkyl which may be substituted by:
  (i) $OR^7$, $NR^5R^6$, $S(O)nR^8$, $HNS(O)nR^8$, or $CO_2R^3$;
  (ii) heterocycle which may be substituted by lower alkyl, $CO_2R^3$, or $S(O)nR^8$;
  (iii) heteroaryl which may be substituted by lower alkyl, $CO_2R^3$, or $S(O)nR^8$; and
  (iv) aryl which may be substituted by lower alkyl, $CO_2R^3$, halogen, $COR^4$ or $NR^5R^6$;
$R^2$ is selected from the group consisting of:
  (i) H;
  (ii) lower alkyl or lower alkyl which may be substituted by OH, $CO_2R^3$, $COR^4$, $CONR^5R^6$, $NR^5R^6$, $OR^7$ (iii) aryl which may be substituted with halogen, $NO_2$, CN, $NR^5R^6$, lower alkyl, lower alkoxy, and lower alkyl substituted by halogen or $OR^7$;
  (iv) heteroaryl which may be substituted by lower alkyl, $CO_2R^3$, $COR^4$, $CONR^5R^6$, $NR^5R^6$, halogen and lower alkyl which may be substituted by $CO_2R^3$, $COR^4$, $CONR^5R^6$, $NR^5R^6$, $OR^7$;
$R^3$ is selected from the group consisting of:
  (i) H;
  (ii) lower alkyl which may be substituted by $OR^7$, $COR^4$, $NR^5R^6$ or $CONR^5R^6$;
  (iii) aryl which may be substituted by up to three substitutents independently selected from the group consisting of lower alkyl, halogen and $NR^5R^6$; and
  (iv) cycloalkyl which may be substituted by OH or $NH_2$;
$R^4$ is selected from the group consisting of:
  (i) H; and
  (ii) lower alkyl which may be substituted by $OR^7$ or $NR^5R^6$;
$R^5$ and $R^6$ are each independently selected from the group consisting of:
  (i) H;
  (ii) lower alkyl which may be substituted by OH, $CO_2R^3$, $CONR^{10}R^{11}$, $SO_2R^3$, $OR^7$, $NR^{10}R^{11}$, heterocycle, or heteroaryl;
  (iii) cycloalkyl which may be substituted by $CO_2R^3$, $CONR^{10}R^{11}$, $SO_2R^4$, $OR^7$, or $NR^{10}R^{11}$;
  (iv) aryl which may be substituted by $CO_2R^3$, $CONR^{10}R^{11}$, $SO_2R^3$, $OR^7$, $NR^{10}R^{11}$, halogen, lower alkyl, and lower alkyl substituted by halogen, $CO_2R3$, $CONR^{10}R^{11}$, $OR^7$, $NR^{10}R^{11}$, or OH;
  (v) $SO_2R^3$;
  (vi) $CO_2R^3$, and
  (vii) $COR^3$; or
alternatively, $NR^5R^6$ can form a ring having a total of 3-7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $NR^5R^6$, lower alkyl, and lower alkyl substituted by $OR^7$;
$R^7$ is selected from the group consisting of H and lower alkyl optionally substituted by $NR^5R^6$ or $OR^9$;
$R^8$ is selected from the group consisting of:
  (i) aryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, and OH;
  (ii) heteroaryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, or OH;
  (iii) $NR^5R^6$;
  (iv) lower alkyl which may be substituted by halogen, $CO_2R^3$, $CONR^5R^6$, $OR^7$, $NR^5R^6$, or OH; and
  (v) heterocycle which may be substituted by $CO_2R^3$, $COR^3$, $SO_2R^3$, $CONR^5R^6$, $OR^7$, or $NR^5R^6$;
$R^9$ is selected from the group consisting of H, lower alkyl, and lower alkyl substituted by OH or halogen;
$R^{10}$ and $R^{11}$ are each independently selected from the group consisting of:
  (i) H;
  (ii) lower alkyl which may be substituted by OH, $CO_2R^3$, $CONR^5R^6$, $SO_2R^3$, $OR^7$, $NR^5R^6$, heterocycle, or heteroaryl;

(iii) cycloalkyl which may be substituted by $CO_2R^3$, $CONR^5R^6$, $SO_2R^3$, $OR^7$, or $NR^5R^6$;
(iv) aryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, or OH;
(v) $SO_2R^3$;
(vi) $CO_2R^3$; and
(vii) $COR^3$; or alternatively, $NR^{10}R^{11}$ can form a ring having a total of 3-7 ring atoms, said ring atoms comprising in addition to the nitrogen to which $R^{10}$ and $R^{11}$ are bonded, carbon ring atoms, said carbon ring atoms optionally being replaced by one or more additional N or O ring atoms or the group $SO_2$, and said ring atoms optionally being substituted by OH, oxo, $NR^5R^6$, lower alkyl and lower alkyl substituted by $OR^7$; and n is 1 or 2.

These compounds inhibit cyclin-dependent kinases, most particularly cyclin-dependent kinase 1 (Cdk1), cyclin-dependent kinase 2 (Cdk2), and cyclin-dependent kinase 4 (Cdk4). These compounds and their pharmaceutically acceptable salts and esters have antiproliferative activity and are useful in the treatment or control of cancer, in particular solid tumors.

The present invention also relates to pharmaceutical compositions comprising one or more compounds of the invention, or a pharmaceutically acceptable salt or ester thereof, and a pharmaceutically acceptable carrier or excipient.

The present invention further relates to a method for treating or controlling cancer, more particularly the treatment or control of a solid tumor, most particularly to the treatment or control of breast, lung and colon and prostate tumors by administering to a patient in need of such therapy a therapeutically effective amount of a compound of formula I, or a pharmaceutically salt or ester thereof.

Finally, this invention also relates to novel intermediate compounds useful in the preparation of a compound of formula I.

DETAILED DESCRIPTION OF THE INVENTION

Definitions

As used herein, the following terms shall have the following definitions.

"Aryl" means a monovalent, monocyclic or bicyclic, aromatic carbocyclic hydrocarbon radical, preferably a 6-10 membered aromatic ring system. Preferred aryl groups include, but are not limited to, phenyl, naphthyl, tolyl and xylyl.

"Carbonyl" means the radical C=O.

"Cycloalkyl" means a non-aromatic, partially or completely saturated monovalent cyclic hydrocarbon radical containing 3 to 8 atoms. Examples of cycloalkyl groups include cyclopropyl, cyclobutyl, cyclopentyl and cyclohexyl.

"Effective amount" means an amount that is effective to prevent, alleviate or ameliorate symptoms of disease or prolong the survival of the subject being treated.

"Halogen" means fluorine, chlorine, bromine or iodine, preferably fluorine or chlorine, more preferably fluorine.

"Hetero atom" means an atom selected from N, O and S.

"Heteroaryl" means an aromatic heterocyclic ring system containing up to two rings. Preferred heteroaryl groups include, but are not limited to, thienyl, furyl, indolyl, pyrrolyl, pyridinyl, pyridine, pyrazinyl, oxazolyl, thiaxolyl, quinolinyl, pyrimidinyl, imidazole, benzofuran and tetrazolyl.

"Heterocycle" or "heterocyclyl" means a saturated or partially unsaturated, non-aromatic cyclic radical of 3 to 8 ring atoms in which from one to 3 ring atoms are hetero atoms selected from nitrogen, oxygen, S(O)n (where n is an integer from 0 to 2), or a combination thereof, the remaining ring atoms being C. Examples of preferred heterocycles are piperidine, piperazine, pyrrolidine, morpholine, indoline, tetrahydropyranyl, thiomorpholino, pentamethylene sulfide, and pentamethylene sulfone.

"$IC_{50}$" refers to the concentration of a particular compound according to the invention required to inhibit 50% of a specific measured activity. $IC_{50}$ can be measured, inter alia, as is described in the Examples, infra.

"$K_I$" refers to a measure of the thermodynamic binding of the ligand/inhibitor (that is, a compound according to the invention) to the target protein. $K_I$ can be measured, inter alia, as is described in the Examples, infra.

"Lower alkyl" alone or in conjunction with another term, e.g. lower alkyl-heterocycle, denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Lower alkoxy" alone or in conjunction with another term, e.g. lower alkoxy-heterocycle, denotes a straight-chain or branched saturated aliphatic alkanol having 1 to 6, preferably 1 to 4, carbon atoms. Typical lower alkoxy groups include methoxy, ethoxy, propoxy, isopropoxy, butoxy, t-butoxy, 2-butoxy, pentoxy, hexoxy and the like.

"Oxo" means =O.

"Pharmaceutically acceptable ester" refers to a conventionally esterified compound of formula I having a carboxyl group, which esters retain the biological effectiveness and properties of the compounds of formula$_1$ and are cleaved in vivo (in the organism) to the corresponding active carboxylic acid. Further information concerning examples of and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

"Therapeutically effective amount" means an amount of at least one compound of Formula I, or a pharmaceutically acceptable salt or ester thereof, that significantly inhibits proliferation and/or prevents differentiation of a human tumor cell, including human tumor cell lines.

In accordance with the present invention, compounds of formula (1) are provided:

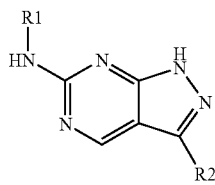

(I)

or the pharmaceutically acceptable salts or esters thereof, wherein
$R^1$ is selected from the group consisting of:
(a) heterocycle which may be substituted by up to four substituents independently selected from the group consisting of:
  (i) lower alkyl which may be substituted by OH, $CO_2R^3$, $COR^4$, $CONR^5R^6$, $NR^5R^6$, $OR^7$, or $S(O)nR^8$; and
  (ii) $CO_2R^3$, $COR^4$, $CONR^5R^6$, $NR^5R^6$, $OR^7$ or $S(O)nR^8$;
(b) aryl which may be substituted by up to four substituents independently selected from the group consisting of:
  (i) $S(O)nR^8$, $NR^5R^6$, lower alkyl, $OR^7$, halogen or lower alkyl which may be substituted by OH, $CO_2R^3$, $COR^4$, $CONR^5R^6$, $NR^5R^6$, $OR^7$;
  (ii) COOH; and
  (iii) carbonyl substituted by lower alkyl, $OR^7$, or $NR^5R^6$;
(c) cycloalkyls which may be substituted by $OR^7$, $NR^5R^6$, or $S(O)nR^8$; and
(d) lower alkyls which may be substituted by:
  (i) $OR^7$, $NR^5R^6$, $S(O)nR^8$, $HNS(O)nR^8$ or $CO_2R^3$;
  (ii) heterocycles which may be substituted by lower alkyl, $CO_2R^3$, or $S(O)nR^8$;
  (iii) heteroaryls which may be substituted by lower alkyl, $CO_2R^3$, or $S(O)nR^8$; and
  (iv) aryls which may be substituted by lower alkyl, $CO_2R^3$, $COR^4$, halogen, or $NR^5R^6$.

Preferably, $R^1$ is a heterocycle selected from the group consisting of piperidine, piperazine, or pyrrolidine; or an aryl selected from the group consisting of phenyl, tolyl, and xylyl; or a cycloalkyl selected from the group consisting of cyclopropyl, cyclobutyl, cyclopentyl, and cyclohexyl; or a lower alkyl selected from the group consisting of methyl, ethyl, propyl, isopropyl, butyl, t-butyl, 2-butyl, pentyl, and hexyl. More preferably, $R^1$ is selected from the group consisting of substituted and unsubstituted piperdine, phenyl, and $C_2$-$C_5$ alkyl groups. More preferably, $R^1$ is substituted by $SO_2CH_3$, $CH_3$, $COOCH_2CH_3$, $SO_2NH_2$, F, $OCH_3$, OH, $NH_2$, or $N(CH_3)_2$.

$R^2$ is selected from the group consisting of:
(i) H;
(ii) lower alkyl or lower alkyl which may be substituted by OH, $CO_2R^3$, $COR^4$, $CONR^5R^6$;
(iii) aryl which may be substituted with halogen, $NO_2$, CN, $NR^5R^6$, lower alkyl, lower alkoxy, and lower alkyl substituted by halogen or $OR^7$.

(iv) heteroaryl which may be substituted by lower alkyl, $CO_2R^3$, $COR^4$, $CONR^5R^6$, $NR^5R^6$, halogen and lower alkyl which may be substituted by $CO_2R^3$, $COR^4$, $CONR^5R^6$, $NR^5R^6$, $OR^7$.

Preferably, $R^2$ is H; or a lower alkyl selected from the group consisting of methyl, ethyl, propyl, isopropyl, butyl, t-butyl, 2-butyl, pentyl, and hexyl; or an aryl selected from the group consisting of phenyl, tolyl, and xylyl. More preferably, $R^2$ is selected from the group consisting of H, methyl, and phenyl which may be substituted with fluorine or methoxy.

$R^3$ is selected from the group consisting of:
(i) H;
(ii) lower alkyl which may be substituted by $OR^7$, $COR^4$, $NR^5R^6$ or $CONR^5R^6$;
(iii) aryl which may be substituted by up to three substitutents independently selected from the group consisting of lower alkyl, halogen and $NR^5R^6$; and
(iv) cycloalkyl which may be substituted by OH or $NH_2$.

Preferably, $R^3$ is H or a lower alkyl selected from the group consisting of methyl, ethyl, propyl, isopropyl, butyl, t-butyl, 2-butyl, pentyl, and hexyl. More preferably, $R^3$ is H, methyl, ethyl, propyl, or isopropyl.

$R^4$ is selected from the group consisting of:
(i) H; and
(ii) lower alkyl which may be substituted by $OR^7$ or $NR^5R$.

Preferably, $R^4$ is H or a lower alkyl selected from the group consisting of methyl, ethyl, propyl, isopropyl, butyl, t-butyl, 2-butyl, pentyl, and hexyl. More preferably, $R^4$ is H, methyl, ethyl, propyl, or isopropyl.

$R^5$ and $R^6$ are each independently selected from the group consisting of:
(i) H;
(ii) lower alkyl which may be substituted by OH, $CO_2R^3$, $CONR^{10}R^{11}$, $SO_2R^3$, $OR^7$, $NR^{10}R^{11}$, heterocycle, or heteroaryl;
(iii) cycloalkyl which may be substituted by $CO_2R^3$, $CONR^{10}R^{11}$, $SO_2R^4$, $OR^7$, or $NR^{10}R^{11}$;
(iv) aryl which may be substituted by $CO_2R^3$, $CONR^{10}R^{11}$, $SO_2R^3$, $OR^7$, $NR^{10}R^{11}$, halogen, lower alkyl, and lower alkyl substituted by halogen, $CO_2R3$, $CONR^{10}R^{11}$, $OR^7$, $NR^{10}R^{11}$, or OH;
(v) $SO_2R^3$;
(vi) $CO_2R^3$, and
(vii) $COR^3$.

Alternatively, $NR^5R^6$ can form a ring having a total of 3-7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $NR^5R^6$, lower alkyl, and lower alkyl substituted by $OR^7$.

Preferably, $R^5$ and $R^6$ are each independently selected from the group consisting of H or a lower alkyl selected from the group consisting of methyl, ethyl, propyl, isopropyl, butyl, t-butyl, 2-butyl, pentyl, and hexyl. More preferably, $R^5$ and $R^6$ are H, methyl, ethyl, propyl, or isopropyl.

$R^7$ is selected from the group consisting of H and lower alkyl optionally substituted by $NR^5R^6$ or $OR^9$.

Preferably, $R^7$ is H or a lower alkyl selected from the group consisting of methyl, ethyl, propyl, isopropyl, butyl, t-butyl, 2-butyl, pentyl, and hexyl. More preferably, $R^7$ is H, methyl, ethyl, propyl, or isopropyl.

R⁸ is selected from the group consisting of:
(i) aryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, and OH;
(ii) heteroaryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, or OH;
(iii) $NR^5R^6$;
(iv) lower alkyl which may be substituted by halogen, $CO_2R^3$, $CONR^5R^6$, $OR^7$, $NR^5R^6$, or OH; and
(v) heterocycle which may be substituted by $CO_2R^3$, $COR^3$, $SO_2R^3$, $CONR^5R^6$, $OR^7$, or $NR^5R^6$.

Preferably, $R^8$ is H or a lower alkyl selected from the group consisting of methyl, ethyl, propyl, isopropyl, butyl, t-butyl, 2-butyl, pentyl, and hexyl. More preferably, $R^8$ is H, methyl, ethyl, propyl, or isopropyl.

$R^9$ is selected from the group consisting of H, lower alkyl, and lower alkyl substituted by OH or halogen.

Preferably, $R^9$ is H or a lower alkyl selected from the group consisting of methyl, ethyl, propyl, isopropyl, butyl, t-butyl, 2-butyl, pentyl, and hexyl. More preferably, $R^9$ is H, methyl, ethyl, propyl, or isopropyl.

$R^{10}$ and $R^{11}$ are each independently selected from the group consisting of:
(i) H;
(ii) lower alkyl which may be substituted by OH, $CO_2R^3$, $CONR^5R^6$, $SO_2R^3$, $OR^7$, $NR^5R^6$, heterocycles, or heteroaryls;
(iii) cycloalkyl which may be substituted by $CO_2R^3$, $CONR^5R^6$, $SO_2R^3$, $OR^7$, or $NR^5R^6$;
(iv) aryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, or OH;
(v) $SO_2R^3$;
(vi) $CO_2R^3$; or
(vii) $COR^3$.

Alternatively, $NR^{10}R^{11}$ can form a ring having a total of 3-7 ring atoms, said ring atoms comprising in addition to the nitrogen to which $R^{10}$ and $R^{11}$ are bonded, carbon ring atoms, said carbon ring atoms optionally being replaced by one or more additional N or O ring atoms or the group $SO_2$, and said ring atoms optionally being substituted by OH, oxo, $NR^5R^6$, lower alkyl and lower alkyl substituted by $OR^7$.

Preferably, $R^{10}$ and $R^{11}$ are each independently selected from the group consisting of H or a lower alkyl selected from the group consisting of methyl, ethyl, propyl, isopropyl, butyl, t-butyl, 2-butyl, pentyl, and hexyl. More preferably, $R^{10}$ and $R^{11}$ are H, methyl, ethyl, propyl, or isopropyl.

Examples of compounds of formula (I) include:
[3-(2,3-Difluoro-6-methoxy-phenyl)-1H-pyrazolo[3,4-d]pyrimidin-6-yl]-(1-methanesulfonyl-piperidin-4-yl)-amine (Example 16)
Methanesulfonyl-piperidin-4-yl)-(1H-pyrazolo[3,4-d]pyrimidin-6-yl)-amine (Example 19)
Methyl-piperidin-4-yl)-(3-methyl-1H-pyrazolo[3,4-d]pyrimidin-6-yl)-amine (Example 23)
[3-(5-Fluoro-2-methoxy-phenyl)-1H-pyrazolo[3,4-d]pyrimidin-6-yl]-(1-methanesulfonyl-piperidin-4-yl)-amine (Example 25)
[3-(5-Fluoro-2-methoxy-phenyl)-1H-pyrazolo[3,4-d]pyrimidin-6-yl]-(1-methanesulfonyl-piperidin-4-yl)-amine (Example 26)
[3-(5-Fluoro-2-methoxy-phenyl)-1H-pyrazolo[3,4-d]pyrimidin-6-yl]-(1-methanesulfonyl-piperidin-4-yl)-amine (Example 27)
(1-Methanesulfonyl-piperidin-4-yl)-[3-(2-methoxy-phenyl)-1H-pyrazolo[3,4-d]pyrimidin-6-yl]-amine; compound with trifluoro-acetic acid (Example 28)
[3-(2,6-Difluoro-phenyl)-1H-pyrazolo[3,4-d]pyrimidin-6-yl]-(1-methanesulfonyl-piperidin-4-yl)-amine (Example 29)
Methanesulfonyl-piperidin-4-yl)-(3-phenyl-1H-pyrazolo[3,4-d]pyrimidin-6-yl)-amine (Example 30)
[3-(3-Fluoro-phenyl)-1H-pyrazolo[3,4-d]pyrimidin-6-yl]-(1-methanesulfonyl-piperidin-4-yl)-amine (Example 31)
4-[3-(2-Methoxy-phenyl)-1H-pyrazolo[3,4-d]pyrimidin-6-ylamino]-benzenesulfonamide; compound with trifluoro-acetic acid (Example 32)
[3-(2,6-Difluoro-phenyl)-1H-pyrazolo[3,4-d]pyrimidin-6-yl]-(4-fluoro-phenyl)-amine (Example 33)
2-[3-(2-Methoxy-phenyl)-1H-pyrazolo[3,4-d]pyrimidin-6-ylamino]-ethanol (Example 34)
[3-(2-Methoxy-phenyl)-1H-pyrazolo[3,4-d]pyrimidin-6-yl]-pentane-1,5-diamine; compound with trifluoro-acetic acid (Example 35)
N'-[3-(2-Methoxy-phenyl)-1H-pyrazolo[3,4-d]pyrimidin-6-yl]-N,N-dimethyl-propane-1,3-diamine (Example 36)
N-[3-(2-Methoxy-phenyl)-1H-pyrazolo[3,4-d]pyrimidin-6-yl]-N,N-dimethyl-pentane-1,5-diamine; compound with trifluoro-acetic acid (Example 37)
[3-(2-Methoxy-phenyl)-1H-pyrazolo[3,4-d]pyrimidin-6-yl]-phenyl-amine (Example 38)
(4-Methoxy-phenyl)-[3-(2-methoxy-phenyl)-1H-pyrazolo[3,4-d]pyrimidin-6-yl]-amine; compound with trifluoro-acetic acid (Example 39)
[3-(2,6-Difluoro-phenyl)-1H-pyrazolo[3,4-d]pyrimidin-6-yl]-(2-methoxy-phenyl)-amine; compound with trifluoro-acetic acid (Example 40)
4-(3-Methyl-1H-pyrazolo[3,4-d]pyrimidin-6-ylamino)-benzenesulfonamide; compound with trifluoro-acetic acid (Example 41)
2-(3-Methyl-1H-pyrazolo[3,4-d]pyrimidin-6-ylamino)-ethanol; compound with trifluoro-acetic acid (Example 42)
4-[3-(3-Fluoro-phenyl)-1H-pyrazolo[3,4-d]pyrimidin-6-ylamino]-piperidine-1-carboxylic acid ethyl ester; compound with trifluoro-acetic acid (Example 43)
Methyl-piperidin-4-yl)-(3-methyl-1H-pyrazolo[3,4-d]pyrimidin-6-yl)-amine (Example 44)

Preferred examples of compounds of formula (I) include:
[3-(2,3-Difluoro-6-methoxy-phenyl)-1H-pyrazolo[3,4-d]pyrimidin-6-yl]-(1-methanesulfonyl-piperidin-4-yl)-amine (Example 16)
Methanesulfonyl-piperidin-4-yl)-(1H-pyrazolo[3,4-d]pyrimidin-6-yl)-amine (Example 19)
[3-(5-Fluoro-2-methoxy-phenyl)-1H-pyrazolo[3,4-d]pyrimidin-6-yl]-(1-methanesulfonyl-piperidin-4-yl)-amine (Example 25)
[3-(5-Fluoro-2-methoxy-phenyl)-1H-pyrazolo[3,4-d]pyrimidin-6-yl]-(1-methanesulfonyl-piperidin-4-yl)-amine (Example 27)
(1-Methanesulfonyl-piperidin-4-yl)-[3-(2-methoxy-phenyl)-1H-pyrazolo[3,4-d]pyrimidin-6-yl]-amine; compound with trifluoro-acetic acid (Example 28)
[3-(3-Fluoro-phenyl)-1H-pyrazolo[3,4-d]pyrimidin-6-yl]-(1-methanesulfonyl-piperidin-4-yl)-amine (Example 31)
4-[3-(2-Methoxy-phenyl)-1H-pyrazolo[3,4-d]pyrimidin-6-ylamino]-benzenesulfonamide; compound with trifluoro-acetic acid (Example 32)

The compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formula above.

General Synthesis of Compounds According to the Invention

The compounds of the present invention can be prepared by any conventional means. Suitable processes for synthesizing these compounds are provided in the examples. Generally, compounds of formula I can be prepared according to one of the below described synthetic routes.

example, the compound can be treated with an inorganic acid such as for example hydrochloric acid, hydrobromic acid, sulfuric acid, nitric acid, phosphoric acid, or with an appropriate organic acid such as acetic acid, citric acid, tartaric acid, methanesulfonic acid, p-toluene sulfonic acid, or the like.

Converting a Compound of Formula I That Bears a Carboxylic Acid Group Into a Pharmaceutically Acceptable Alkali Metal Salt The optional conversion of a compound of formula I that bears a carboxylic acid group into a pharmaceutically acceptable alkali metal salt can be effected by conventional means.

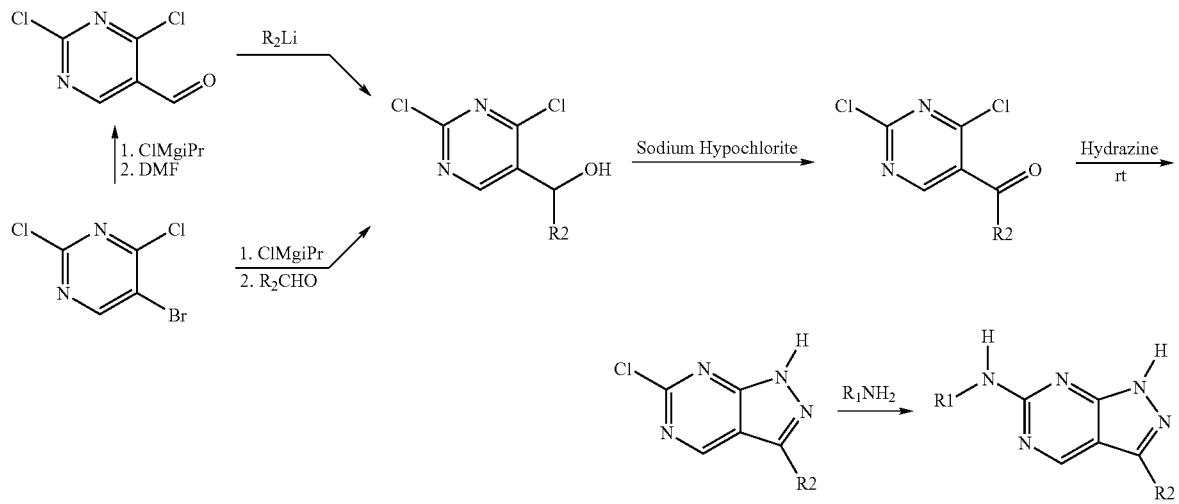

Generally, these compounds may be prepared according to the synthetic schemes provided above. Suitable processes for the preparation of these compounds are given in the examples.

Separating a Mixture of Stereoisomers Into the Optically Pure Stereoisomers (When Compound of Formula I is Chiral)

The optional separation of isomeric structures of formula I can be carried out according to known methods such as for example resolution or chiral high pressure liquid chromatography (also known as chiral HPLC). Resolution methods are well known, and are summarized in "Enantiomers, Racemates, and Resolutions" (Jacques, J. et al. John Wiley and Sons, NY, 1981). Methods for chiral HPLC are also well known, and are summarized in "Separation of Enantiomers by Liquid Chromatographic Methods" (Pirkle, W. H. and Finn, J. in "Asymmetric Synthesis", Vol. 1, Morrison, J. D., Ed., Academic Press, Inc., NY 1983, pp. 87-124).

Converting a Compound of Formula I That Bears a Basic Nitrogen Into a Pharmaceutically Acceptable Acid Addition Salt The optional conversion of a compound of formula I that bears a basic nitrogen into a pharmaceutically acceptable acid addition salt can be effected by conventional means. For For example, the compound can be treated with an inorganic base such as lithium hydroxide, sodium hydroxide, potassium hydroxide, or the like.

Converting a Compound of Formula I That Bears a Carboxylic Acid Group Into a Pharmaceutically Acceptable Ester The optional conversion of a compound of formula I that bears a carboxylic acid group into a pharmaceutically acceptable ester can be effected by conventional means. The conditions for the formation of the ester will depend on the stability of the other functional groups in the molecule to the reaction conditions. If the other moieties in the molecule are stable to acidic conditions, the ester may be conveniently prepared by heating in a solution of a mineral acid (e.g., sulfuric acid) in an alcohol. Other methods of preparing the ester, which may be convenient if the molecule is not stable to acidic conditions include treating the compound with an alcohol in the presence of a coupling agent and in the optional presence of additional agents that may accelerate the reaction. Many such coupling agents are known to one skilled in the art of organic chemistry. Two examples are dicyclohexylcarbodiimide and triphenylphosphine/diethyl azodicarboxylate. In the case where dicyclohexylcarbodiimide is used as the coupling agent, the reaction is conveniently carried out by treating the acid with the alcohol, dicyclohexylcarbodiimide, and the optional presence of a catalytic amount (0-10 mole %) of N,N-dimethylaminopyridine, in an inert solvent such as a halogenated hydrocarbon (e.g., dichloromethane) at a temperature between about 0° C. and about room temperature, preferably at about room temperature. In the case where triphenylphosphine/diethyl azodicarboxylate is used as the coupling agent, the reaction is conveniently carried out by treating the acid with the alcohol, triphenylphosphine and diethyl azodicarboxylate, in an inert solvent such as an ether (e.g., tetrahydrofuran) or an aromatic hydrocarbon (e.g., benzene) at a temperature between about 0° C. and about room temperature, preferably at about 0° C.

Compositions/Formulations

In an alternative embodiment, the present invention includes pharmaceutical compositions comprising at least one compound of formula (I), or a pharmaceutically acceptable salt or ester thereof and a pharmaceutically acceptable excipient and/or carrier.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions. The pharmaceutical compositions of the present invention comprising compounds of formula I, and/or the salts or esters thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula (I).

Dosages

As mentioned above, the compounds of the present invention, including the compounds of formula (I), are useful in the treatment or control of cell proliferative disorders, including chemoprevention of cancer. Chemoprevention is defined as inhibiting the development of invasive cancer by either blocking the initiating mutagenic event or by blocking the progression of pre-malignant cells that have already suffered an insult of inhibiting tumor relapse. These compounds and formulations containing said compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Combinations

The compounds of this invention may be used in combination (administered in combination or sequentially) with known anti-cancer treatments such as radiation therapy or with cytostatic or cytotoxic agents, such as for example, but not limited to, DNA interactive agents, such as cisplatin or doxorubicin; topoisomerase 11 inhibitors such as etoposide: topoisomerase I inhibitors such as CPT-11 or topotecan; tublin interacting agents, such as paclitaxel, docetaxel or epothilones; hormonal agents such as tamoxifen: thymidilate synthase inhibitors, such as 5-fluorouracil; and anti-metabolites such as methotrexate. Compounds of formula I may also be useful in combination with modulators of p53 transactivation.

If formulated as a fixed dose, the above-described combination products include the compounds of this invention within the dosage range described above and the other pharmaceutically active agent or treatment within its approved dose range. For example, an early Cdk1 inhibitor olomucine has been found to act synergistically with well known cytotoxic agents in inducing apoptosis. (*J. Cell Sci.,* 1995, 108, 2897-2904). Compounds of formula I may also be administered sequentially with known anticancer or cytoxic agents when concomitant administration or a combination is inappropriate. This invention is not limited in the sequence of administration: compounds of formula I may be administered either prior to or after administration of the known anticancer or cytotoxic agent. For example, the cytotoxic activity of the Cdk inhibitor flavopiridol is affected by the sequence of administration with anticancer agents. (*Cancer Research,* 1997, 57, 3375).

EXAMPLES

The following examples illustrate preferred methods for synthesizing and using the compounds and formulations of the present invention. These examples and preparations are illustrative and are not intended to be limiting. It should be understood that there may be other embodiments which fall within the spirit and scope of the invention as defined by the claims appended hereto.

Example 1

(2,4-Dichloro-pyrimidin-5-yl)-(2,3-difluoro-6-methoxy-phenyl)-methanol

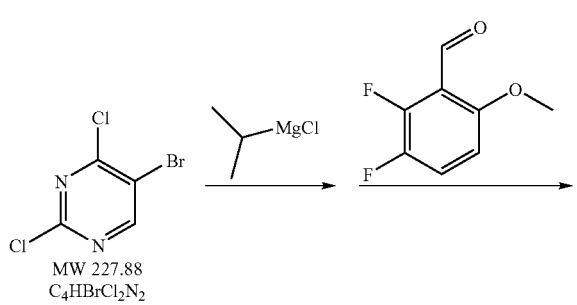

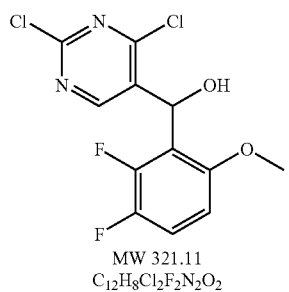

To a stirred solution of 5-bromo-2,4-dichloropyrimidine (Aldrich, 3.02 g, 13.25 mmol) in 20 mL of THF at −30° C., isopropyl magnesium chloride (Aldrich, 2M solution in THF, 7.12 mL, 13.25 mmol) was added dropwise and the mixture was stirred for 20 minutes. Then 2,3-difluoro-6-methoxybenzaldehyde (Matrix, 2.28 g, 13.25 mmol) was added and the mixture was warmed to 0° C. and stirred for 40 minutes. The reaction was quenched with saturated ammonium chloride solution and the resulting mixture was extracted with EtOAc. The extract was dried with sodium sulfate. The solvent was removed on a rotary evaporator and the solid was treated with hexane (8 mL). The solid was filtered and dried to give an off-white solid. 3.42 g; Yield, 80.5%. MS (M+H)+, 322.

Example 2

(2,4-Dichloro-pyrimidin-5-yl)-(2,3-difluoro-6-methoxy-phenyl)-methanone

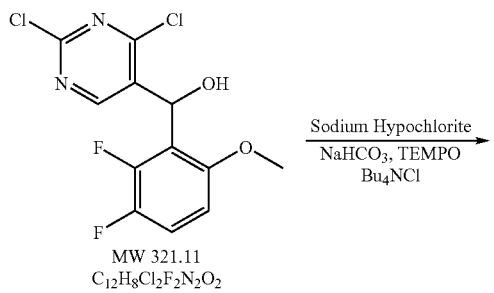

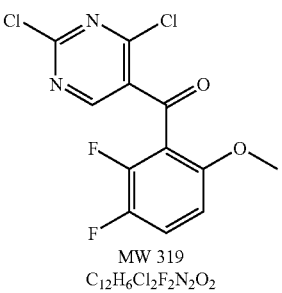

The alcohol (2.00 g, 6.23 mmol) was dissolved in methylene chloride (20 mL). To the stirred solution, water (2 mL) was added followed by NaHCO3 (235 mg, 2.8 mmol), tetrabutylammonium chloride (Aldrich, 60 mg, 0.18 mmol) and TEMPO (Aldrich, 10 mg, 0.062 mmol). The mixture was then cooled to 0° C. and sodium hypochlorite (Aldrich, active Cl2, 5.8%, 8.78 mL) was added slowly and the resulting new mixture was stirred for 30 minutes. The mixture was poured into water and extracted with methylene chloride. The extract was dried with sodium sulfate. Removal of solvent gave the right product as a pale yellow solid. 1.84 g, 92%. MS (M+H)+, 319.

Example 3

6-Chloro-3-(2,3-difluoro-6-methoxy-phenyl)-1H-pyrazolo[3,4-d]pyrimidine

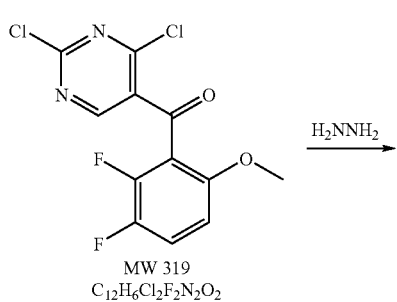

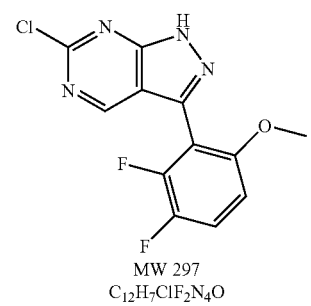

To a stirred solution of ketone (638 mg, 2 mmol) in THF, hydrazine (Aldrich, 80 mg, 2.5 mmol) was added and the mixture was stirred for 30 minutes at room temperature and then at 50° C. for 1 hour. The solvent was removed and the solid was washed with water and dried to give a yellow solid. 580 mg, 97%. MS (M+H)+, 297.

Example 4

(2,4-Dichloro-pyrimidin-5-yl)-(2-methoxy-phenyl)-methanol

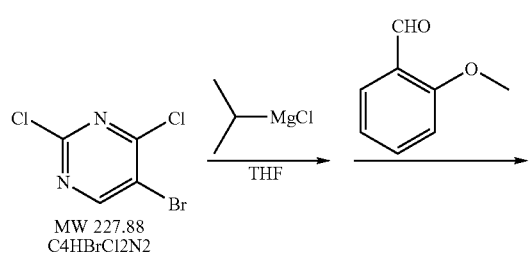

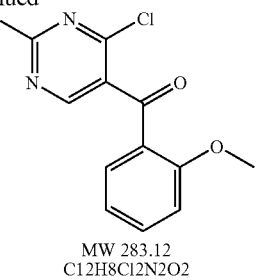

MW 285.13
C12H10Cl2N2O2

The compound was prepared from 5-bromo-2,4-dichloro-pyrimidine (Aldrich) and 2-methoxybenzaldehyde (Aldrich) in 77% yield in an analogous manner as described in Example 1. 1H NMR (300 MHz, CDCl3) δ 8.75 (s,1 H), 7.34 (d.t. 1H, J=2 Hz, 8 Hz), 7.16 (d,d, 1H, J=1.8 Hz, 7.3 Hz ), 6.96 (d, 1H, J=7.3 Hz), 6.95 (d,1H, J=8 Hz), 1H), 3.85 (s, 3H), 3.148 (br. s, 1H).

Example 5

(2,4-Dichloro-pyrimidin-5-yl)-(2-methoxy-phenyl)-methanone

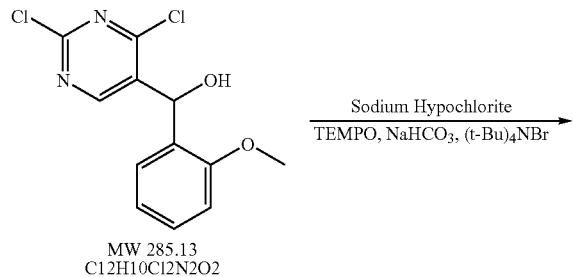

MW 285.13
C12H10Cl2N2O2

MW 283.12
C12H8Cl2N2O2

The compound was prepared from (2,4-dichloro-pyrimidin-5-yl)-(2-methoxy-phenyl)-methanol (Example 4) in 96% yield in an analogous manner as described in Example 2. 1H NMR (300 MHz, CDCl3) δ 8.60 (s, 1H), 7.84 (d, d, 1H, J =2 Hz, 8 Hz), 7.60 (dd, 1H, J=2 Hz, 7.3 Hz), 7.12 (d, 1H, J=7.3 Hz), 6.95 (d, 1H, J=8 Hz), 3.67 (s, 3H)

Example 6

6-Chloro-3-(2-methoxy-phenyl)-1H-pyrazolo[3,4-d]pyrimidine

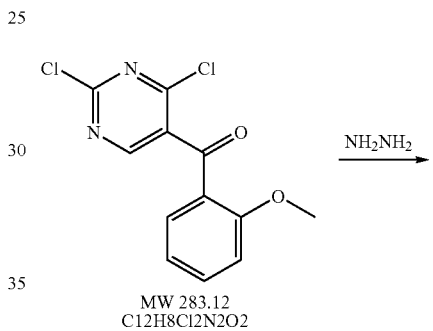

MW 283.12
C12H8Cl2N2O2

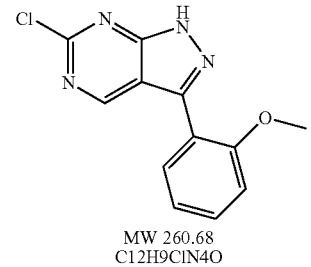

MW 260.68
C12H9ClN4O

The compound was prepared from (2,4-dichloro-pyrimidin-5-yl)-(2-methoxy-phenyl)-methanone (Example 5) in 35% yield in an analogous manner as described in Example 3. MS (M+H)+, 261.11.

Example 7

(2,4-Dichloro-pyrimidin-5-yl)-(3-fluoro-phenyl)-methanol

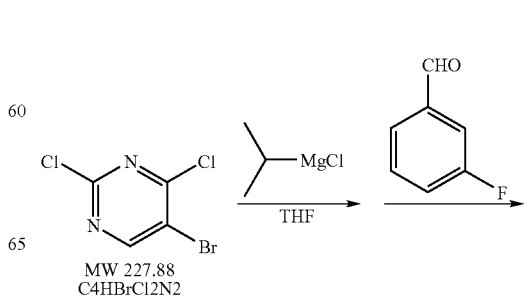

MW 227.88
C4HBrCl2N2

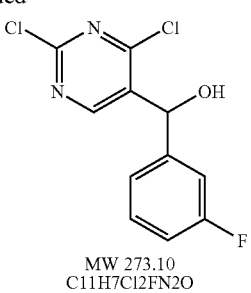

MW 273.10
C11H7Cl2FN2O

The compound was prepared from 5-bromo-2,4-dichloro-pyrimidine (Aldrich) and 3-fluorobenzaldehyde (Aldrich) in 79% yield in an analogous manner as described in Example 1. 1H NMR (300 MHz, CDCl3) δ 8.85 (s, 1H), 7.35 (m, 1H), 7.14 (m, 3H), 7.14 (m, 3H), 6.077 (s, 1H).

Example 8

(2,4-Dichloro-pyrimidin-5-yl)-(3-fluoro-phenyl)-methanone

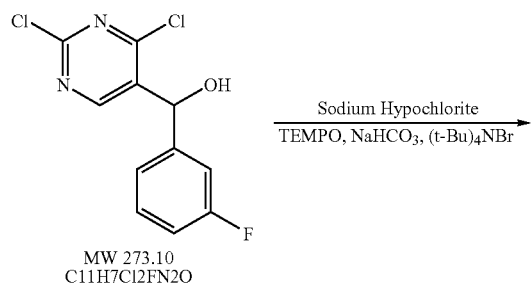

MW 273.10
C11H7Cl2FN2O

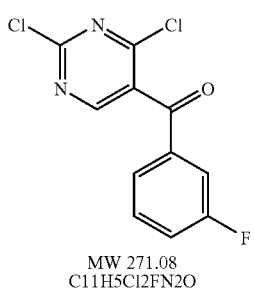

MW 271.08
C11H5Cl2FN2O

The compound was prepared from (2,4-dichloro-pyrimidin-5-yl)-(3-fluoro-phenyl)-methanol (Example 7) in 99% yield in an analogous manner as described in Example 2. 1H NMR (300 MHz, CDCl3) δ 8.632 (s, 1H), 7.52 (m, 4H), 7.43 (m, 1H), 5.303 (s, 1H).

Example 9

6-Chloro-3-(3-fluoro-phenyl)-1H-pyrazolo[3,4-d]pyrimidine

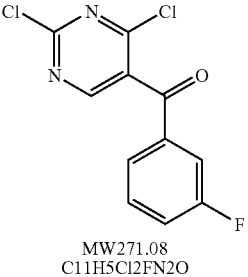

MW 271.08
C11H5Cl2FN2O

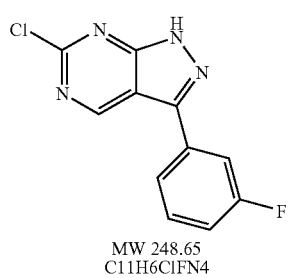

MW 248.65
C11H6ClFN4

The compound was prepared from (2,4-dichloro-pyrimidin-5-yl)-(3-fluoro-phenyl)-methanone (Example 8) in 75% yield in an analogous manner as described in Example 3. MS (M+H)+, 249.

Example 10

(2,4-Dichloro-pyrimidin-5-yl)-(2,6-difluoro-phenyl)-methanol

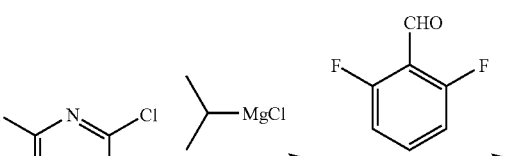

MW 227.88
C4HBrCl2N2

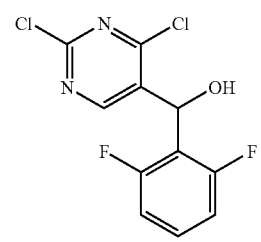

MW 291.09
C11H6Cl2F2N2O

The compound was prepared from 5-bromo-2,4-dichloro-pyrimidine (Aldrich) and 2,6-difluorobenzaldehyde (Aldrich) in 88% yield in an analogous manner as described in Example 1. 1H NMR (300 MHz, CDCl3) δ 9.09 (s, 1H), 7.35 (m, 1H, 7.92 (m, 2H), 6.35 (s, 1H), 2.67 (br. s, 1H).

Example 11

(2,4-Dichloro-pyrimidin-5-yl)-(2,6-difluoro-phenyl)-methanone

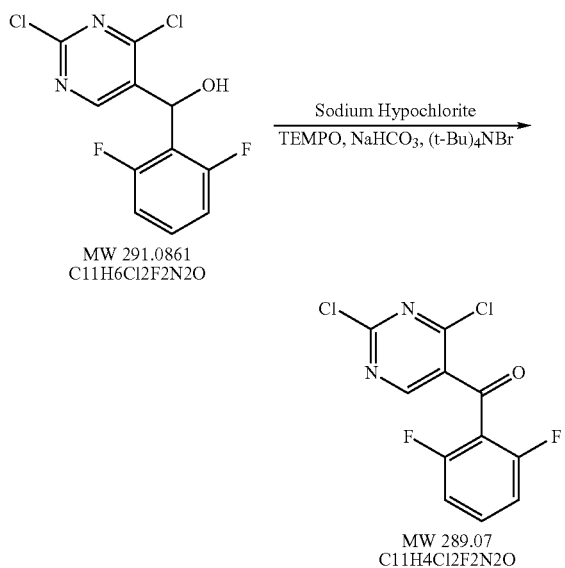

The compound was prepared from (2,4-dichloro-pyrimidin-5-yl)-(2,6-difluoro-phenyl)-methanol (Example 10) in 98% yield in an analogous manner as described in Example 2. 1H NMR (300 MHz, CDCl3) δ 8.79 (s, 1H), 7.56 (m, 1H), 7.04 (m, 2H).

Example 12

6-Chloro-3-(2,6-difluoro-phenyl)-1H-pyrazolo[3,4-d]pyrimidine

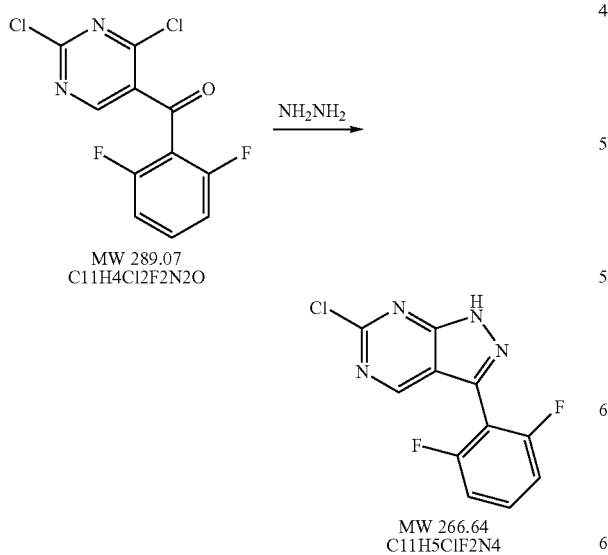

The compound was prepared from (2,4-dichloro-pyrimidin-5-yl)-(2,6-difluoro-phenyl)-methanone (Example 11) in 71% yield in an analogous manner as described in Example 3. MS (M+H)+, 267.08.

Example 13

(2,4-Dichloro-pyrimidin-5-yl)-phenyl-methanol

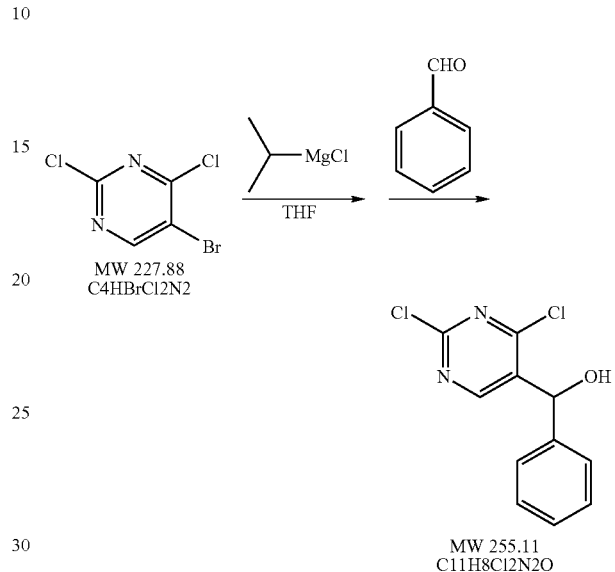

The compound was prepared from 5-bromo-2,4-dichloro-pyrimidine (Aldrich) and benzaldehyde (Aldrich) in 79% yield in an analogous manner as described in Example 1. 1H NMR (300 MHz, CDCl3) δ 8.91 (s, 1H), 7.36 (m, 5H), 6.06 (d, 1H, J=3.0 Hz), 2.48 (br m,1H).

Example 14

(2,4-Dichloro-pyrimidin-5-yl)-phenyl-methanone

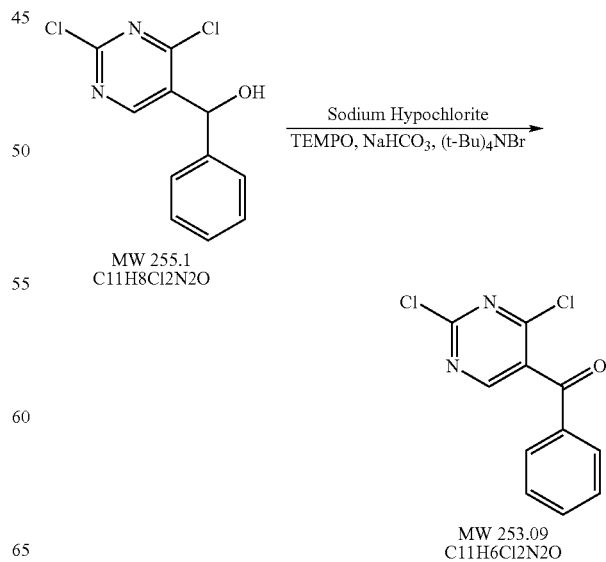

The compound was prepared from (2,4-dichloro-pyrimidin-5-yl)-phenyl-methanol (Example 13) in 98% yield in an analogous manner as described in Example 2. 1H NMR (300 MHz, CDCl3) δ 8.62 (s, 1H), 7.79 (m, 2H), 7.70 (m, 1H), 7.54 (m, 2H).

Example 15

6-Chloro-3-phenyl-1H-pyrazolo[3,4-d]pyrimidine

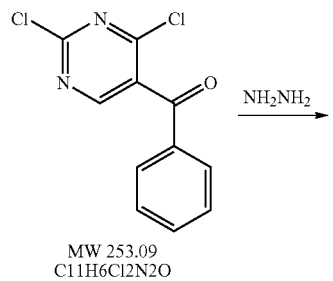

MW 253.09
C11H6Cl2N2O

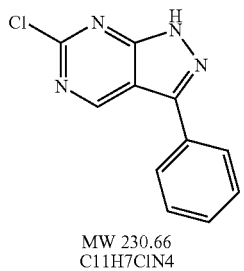

MW 230.66
C11H7ClN4

The compound was prepared from (2,4-dichloro-pyrimidin-5-yl)-phenyl-methanone (Example 14) in 99% yield in an analogous manner as described in Example 3. MS (M+H)+, 231.08.

Example 16

[3-(2,3-Difluoro-6-methoxy-phenyl)-1H-pyrazolo[3,4-d]pyrimidin-6-yl]-(1-methanesulfonyl-piperidin-4-yl)-amine

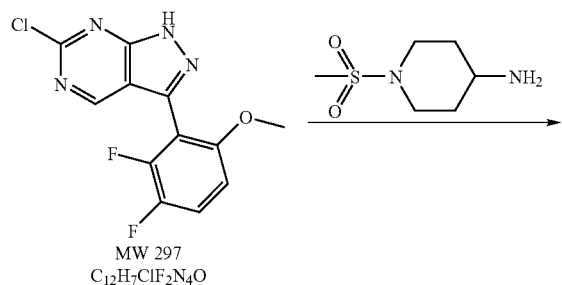

MW 297
C12H7ClF2N4O

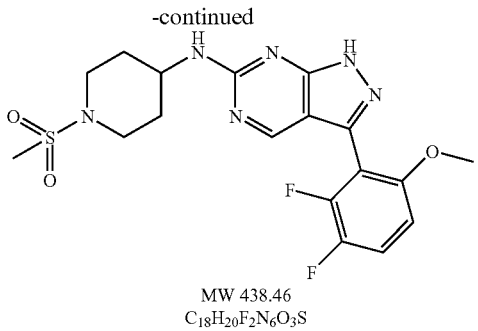

MW 438.46
C18H20F2N6O3S

To a stirred solution of 6-chloro-3-(2,3-difluoro-6-methoxy-phenyl)-1H-pyrazolo[3,4-d]pyrimidine (Example 3, 148 mg, 0.50 mmol) in DMF (2.5 mL), sodium bicarbonate (100 mg) and 1-methanesulfonyl-piperidin-4-ylamine, 125 mg, 0.70 mmol) were added and the mixture was stirred at 100° C. for 4 hours. The solvent was removed under reduced pressure and the residue was treated with water. The solid was filtered and dried. Recrystallization from 2% MeOH/CH2Cl2 gave 92 mg off-white solid. 42%. MS (M+H)+, 439.

Example 17

2,4-Dichloro-pyrimidine-5-carbaldehyde

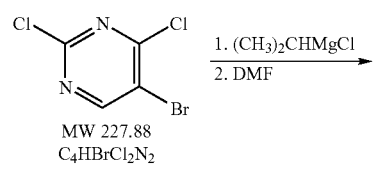

MW 227.88
C4HBrCl2N2

MW 176
C5H2BrCl2N2

To a stirred solution of 5-bromo-2,4-dichloropyrimidine (Aldrich, 454 mg, 2 mmol) in THF at −78° C., diisopropyl magnesium chloride (2M solution in THF, 2.1 mmol, 1.05 mL) was added and the mixture was stirred for 30 minutes at −35° C. Next, the solution was cooled to −78° C. and 1 mL of dry DMF was added. The mixture was stirred for 120 minutes at −78° C. and the reaction was quenched with 1 N HCl. The mixture was extracted with EtOAc and dried with sodium sulfate. The solvent was removed and the residue was chromatographed to give a brown solid. 102 mg, 28%. H1NMR (CDCl3), δ (ppm), 9.0 (s, 1 H), 10.4 (s, 1 H).

Example 18

6-Chloro-1H-pyrazolo[3,4-d]pyrimidine

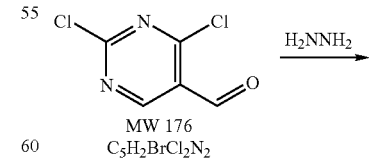

MW 176
C5H2BrCl2N2

MW 154.56
C5H3ClN4

To a stirred solution of hydrazine (Aldrich, 64 mg, 2 mmol) in THF (5 mL), 2,4-Dichloro-pyrimidine-5-carbaldehyde (Example 17, 176 mg, 1 mmol) was added and the mixture was stirred at room temperature for 30 min. The mixture was poured into water and extracted with EtOAc. The extract was dried with sodium sulfate and the solvent was removed to give an orange solid. 128 mg, 82%. MS (M+H)+, 155.

Example 19

Methanesulfonyl-piperidin-4-yl)-(1H-pyrazolo[3,4-d]pyrimidin-6-yl)-amine

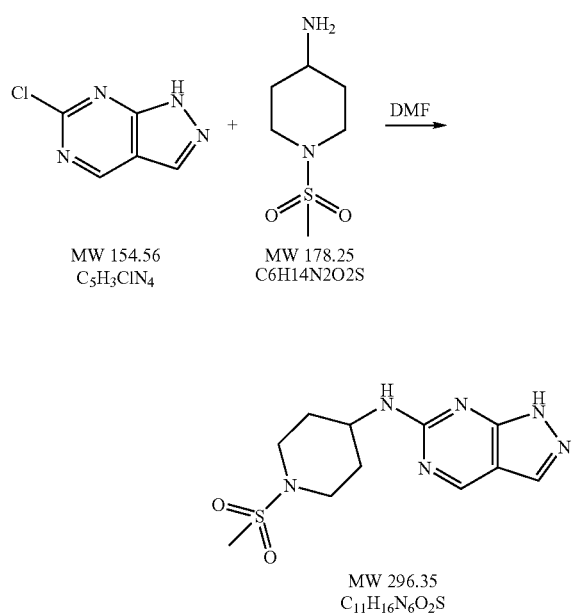

To a stirred solution of (1-methanesulfonyl-piperidin4-yl)-(1H-pyrazolo[3,4-d]pyrimidin-6-yl)-amine (Example 18, 61 mg, 0.40 mmol) in DMF (2.5 mL), sodium bicarbonate (60 mg) and 1-methanesulfonyl-piperidin-4-ylamine(85 mg, 0.48 mmol) were added and the mixture was stirred at 100° C. for 5 hours. The solvent was removed under reduced pressure and the residue was treated with water and the mixture was extracted with EtOAc. The extract was dried with sodium sulfate and concentrated to give a solid, which was purified by reverse phase HPLC to give an off-white solid. 29 mg, 29%. MS (M+H)+, 297.

Example 20

1-(2,4-Dichloro-pyrimidin-5-yl)-ethanol

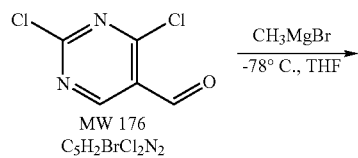

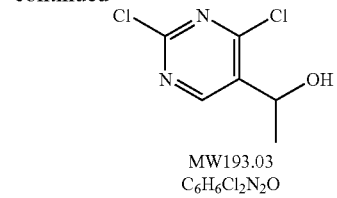

To a stirred solution of 2,4-dichloro-pyrimidine-5-carbaldehyde (Example 17, 1.01 g, 5.7 mmol) in THF (10 mL), methyl magnesium bromide (Aldrich, 3 M in ether, 6.27 mmol, 2.1 mL) was added slowly at −78° C. The mixture was stirred for an additional 2 hours at −78° C. and the reaction was quenched with 1N HCl (10 mL). The resulting mixture was extracted with EtOAc and the extract was dried with sodium sulfate. Removal of solvent gave a brown solid. 1.07 g, 97%. MS (M+H)+, 193.

Example 21

1-(2,4-Dichloro-pyrimidin-5-yl)-ethanone

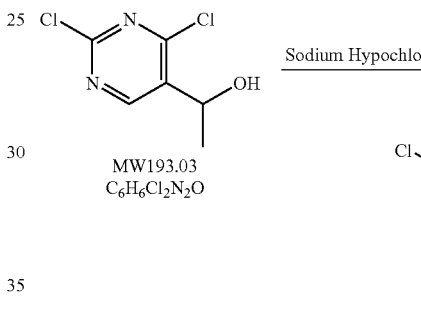

To a stirred suspension of 1-(2,4-dichloro-pyrimidin-5-yl)-ethanol (Example 20, 1.00 g, 5.2 mmol) in a mixture of methylene chloride (30 mL), THF (8 mL) and water (2 mL), tetrabutylammonium chloride (Aldrich, 50 mg, 0.15 mmol), TEMPO (Aldrich, 9 mg, 0.05 mmol) and sodium bicarbonate (208 mg, 2.48 mmol) were added and the mixture was cooled to 0° C. To the stirred mixture, colorex (Aldrich; active Cl$_2$, 10-13%; 3.75 mL) was added and the mixture was stirred for 2 hours at 0° C. Water (10 mL) was added and the organic layer was separated and dried over sodium sulfate. Removal of solvent gave an oil which was purified by silica gel chromatography (1% MeOH/CH2Cl2) to yield a colorless oil. 232 mg, 23%. MS (M+H)+, 191.

Example 22

6-Chloro-3-methyl-1H-pyrazolo[3,4-d]pyrimidine

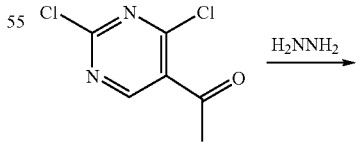

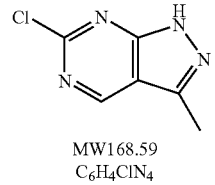

To a stirred solution of hydrazine (Aldrich, 102.4 mg, 3.2 mmol) in THF (5 mL), 1-(2,4-dichloro-pyrimidin-5-yl)-ethanone (Example 21, 191 mg, 1 mmol) was added and the mixture was stirred at room temperature for 1 hour. The reaction was quenched with water (5 mL) and the mixture was extracted with EtOAc/THF(3×5 mL, 1:1 mixture of EtOAc: THF ). The extract was dried with sodium sulfate and concentrated to give a solid. 126 mg, 75%. MS (M+H)+, 169.

Example 23

Methyl-piperidin-4-yl)-(3-methyl-1H-pyrazolo[3,4-d]pyrimidin-6-yl)-amine

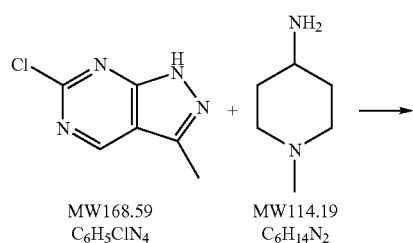

To a stirred solution of 6-chloro-3-methyl-1H-pyrazolo[3,4-d]pyrimidine (Example 22, 56 mg, 0.3 mmol) in DMF (1.5 mL), 1-methyl-piperidin-4-ylamine (Aldrich, 46 mg, 0.40 mmol) was added and the mixture was stirred at 100° C. for 2 hours. The solvent was removed and the residue was chromatographed (5% 7N ammonia in MeOH/CH2Cl2) to give a white solid. 45 mg, 61%. MS (M+H)+, 247.

Example 24

6-Chloro-3-(5-fluoro-2-methoxy-phenyl)-1H-pyrazolo[3,4-d]pyrimidine

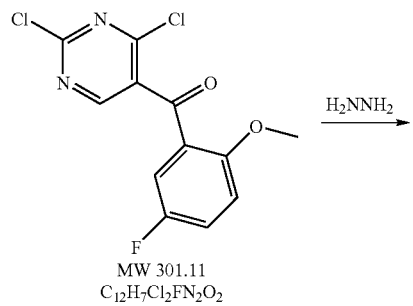

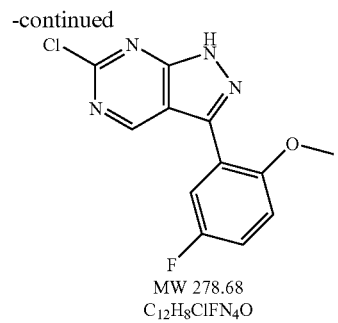

To a stirred solution of (2,4-dichloro-pyrimidin-5-yl)-(5-fluoro-2-methoxy-phenyl)-methanone (602 mg, 2 mmol) in THF (8 m), hydrazine (Aldrich, 98%, 64 mg, 2 mmol) was added and the mixture was stirred for 20 minutes followed by a second portion of hydrazine (0.1 mL). The reaction finished in 5 minutes. The solvent was removed and the solid was washed with water/acetonitrile (3:1) to give a yellow solid. 456 mg, 82%. MS (M+H)+, 278.

Example 25

[3-(5-Fluoro-2-methoxy-phenyl)-1H-pyrazolo[3,4-d]pyrimidin-6-yl]-(1-methanesulfonyl-piperidin-4-yl)-amine

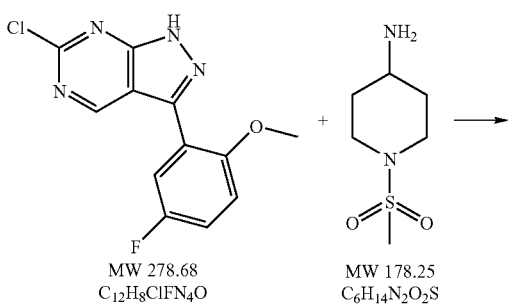

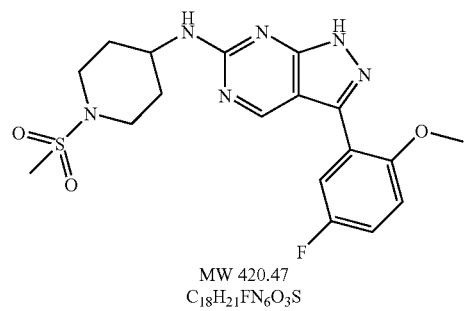

To a stirred solution of 6-chloro-3-(5-fluoro-2-methoxy-phenyl)-1H-pyrazolo[3,4-d]pyrimidine (Example 24, 97 mg, 0.35 mmol) in DMF (4 mL), sodium bicarbonate (60 mg) and 1-methanesulfonyl-piperidin-4-ylamine (93 mg, 0.52 mmol) were added and the mixture was stirred at 100° C. for 4 hours. The reaction was cooled and the mixture was poured into water (60 mL). The solid was filtered and dried to give a yellow solid, which was purified by reverse phase HPLC to give 52 mg pale yellow solid. Yield, 35%. MS (M+H)+, 421.

Example 26

[3-(5-Fluoro-2-methoxy-phenyl)-1H-pyrazolo[3,4-d]pyrimidin-6-yl]-(1-methanesulfonyl-piperidin-4-yl)-amine

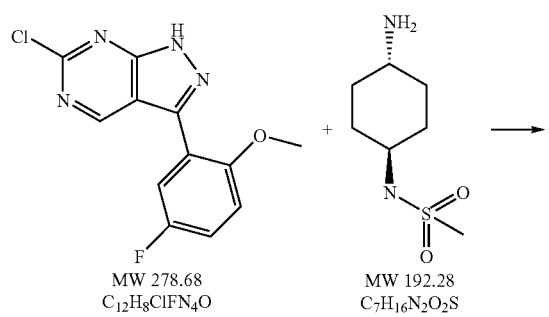

MW 278.68  
C₁₂H₈ClFN₄O

MW 192.28  
C₇H₁₆N₂O₂S

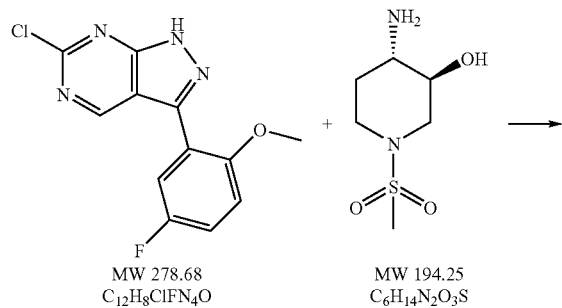

MW 434.4960  
C₁₉H₂₃FN₆O₃S

The same procedure as described in Example 25 was used starting from 6-chloro-3-(5-fluoro-2-methoxy-phenyl)-1H-pyrazolo[3,4-d]pyrimidine, Example 24, (97 mg, 0.35 mmol), and N-(4-amino-cyclohexyl)-methanesulfonamide, (101 mg, 0.52 mmol), to give a yellow solid. 70 mg, 46%. MS (M+H)+, 435.

Example 27

[3-(5-Fluoro-2-methoxy-phenyl)-1H-pyrazolo[3,4-d]pyrimidin-6-yl]-(1-methanesulfonyl-piperidin-4-yl)-amine

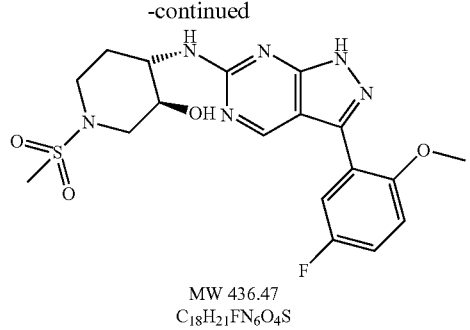

MW 278.68  
C₁₂H₈ClFN₄O

MW 194.25  
C₆H₁₄N₂O₃S

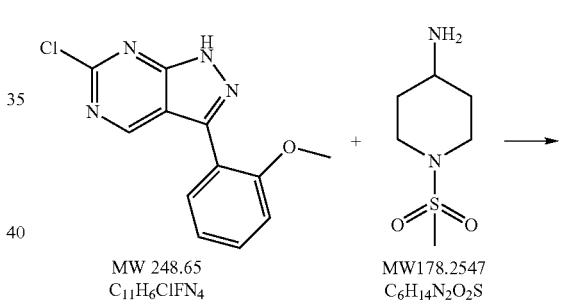

MW 436.47  
C₁₈H₂₁FN₆O₄S

The same procedure as described in Example 25 was used starting from 6-chloro-3-(5-fluoro-2-methoxy-phenyl)-1H-pyrazolo[3,4-d]pyrimidine, Example 24, (103 mg, 0.37 mmol), and (3S,4S)-4-amino-1-methanesulfonyl-piperidin-3-ol, (115 mg, 0.59 mmol), to give a yellow solid. 70 mg, 46%. MS (M+H)+, 437.

Example 28

Methanesulfonyl-piperidin-4-yl)-[3-(2-methoxy-phenyl)-1H-pyrazolo[3,4-d]pyrimidin-6-yl]-amine; compound with trifluoro-acetic acid

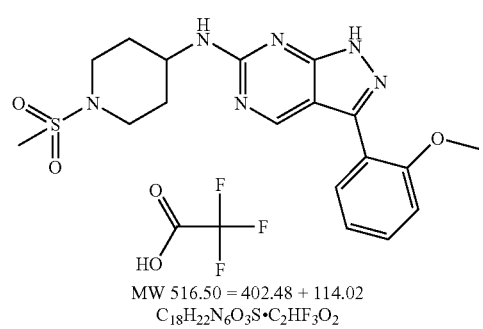

MW 248.65  
C₁₁H₆ClFN₄

MW178.2547  
C₆H₁₄N₂O₂S

MW 516.50 = 402.48 + 114.02  
C₁₈H₂₂N₆O₃S·C₂HF₃O₂

The compound was prepared from 6-chloro-3-(2-methoxy-phenyl)-1H-pyrazolo[3,4-d]pyrimidine (Example 6) and 1-methanesulfonyl-piperidin-4-ylamine, compound with trifluoro-acetic acid in an analogous manner as described in Example 4 and was purified by HPLC to obtain a TFA salt (36% yield). MS (M+H)+, 403.24.

Example 29

[3-(2,6-Difluoro-phenyl)-1H-pyrazolo[3,4-d]pyrimidin-6-yl]-(1-methanesulfonyl-piperidin-4-yl)-amine

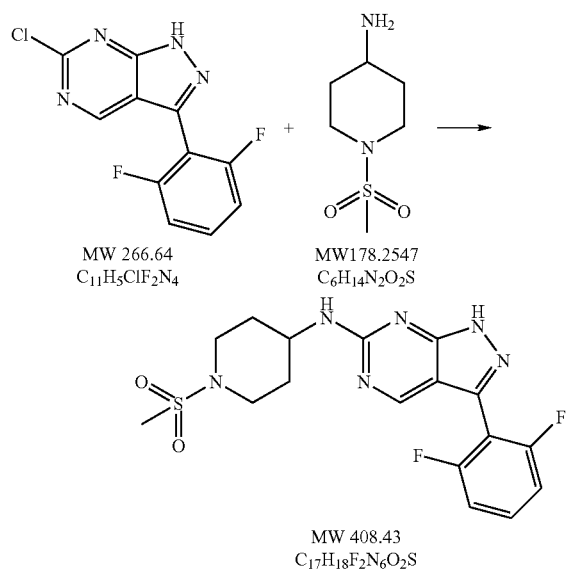

The compound was prepared from 6-chloro-3-(2,6-difluoro-phenyl)-1H-pyrazolo[3,4-d]pyrimidine (Example 8) and 1-methanesulfonyl-piperidin-4-ylamine; compound with trifluoro-acetic acid in an analogous manner as described in Example 4 and was purified by HPLC (Gilson) to give a free base (34.5% yield). MS (M+H)+, 409.22.

Example 30

(1-Methanesulfonyl-piperidin-4-yl)-(3-phenyl-1H-pyrazolo[3,4-d]pyrimidin-6-yl)-amine

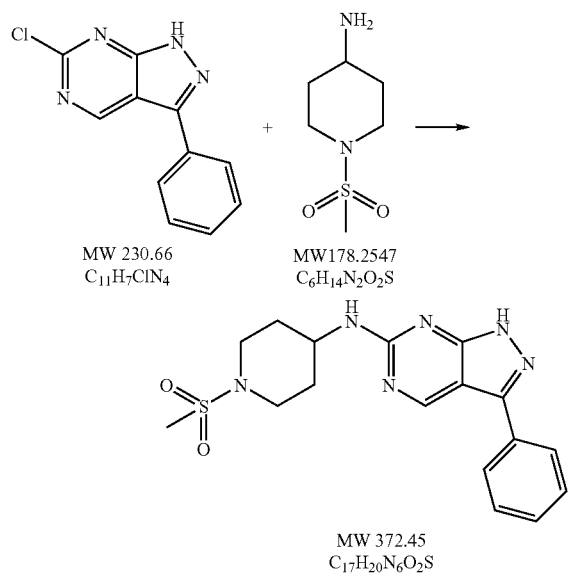

The compound was prepared from 6-chloro-3-phenyl-1H-pyrazolo[3,4-d]pyrimidine (Example 14) and 1-methanesulfonyl-piperidin-4-ylamine; compound with trifluoro-acetic acid in an analogous manner as described in Example 4 and was purified by HPLC (Gilson) to give a free base (21% yield). MS (M+H)+, 373.24.

Example 31

[3-(3-Fluoro-phenyl)-1H-pyrazolo[3,4-d]pyrimidin-6-yl]-(1-methanesulfonyl-piperidin-4-yl)-amine

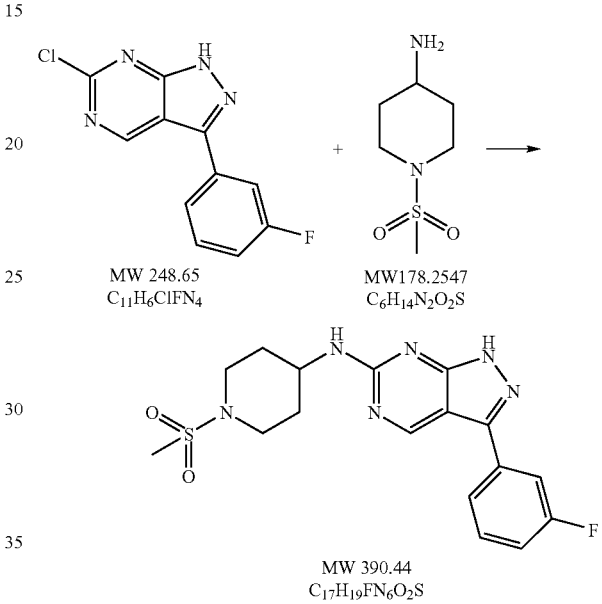

The compound was prepared from 6-chloro-3-(3-fluoro-phenyl)-1H-pyrazolo[3,4-d]pyrimidine (Example 9) and 1-methanesulfonyl-piperidin-4-ylamine; compound with trifluoro-acetic acid in an analogous manner as described in Example 4 and was purified by HPLC (Gilson) to give a free base (6% yield). MS (M+H)+, 391.25.

Example 32

4-[3-(2-Methoxy-phenyl)-1H-pyrazolo[3,4-d]pyrimidin-6-ylamino]-benzenesulfonamide; compound with trifluoro-acetic acid

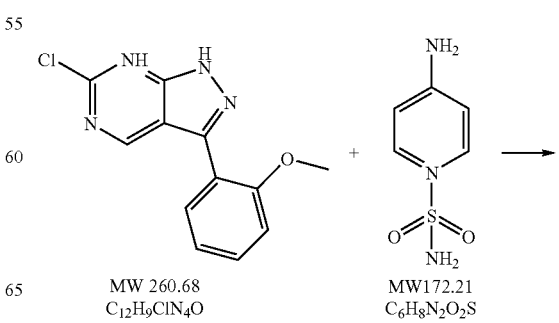

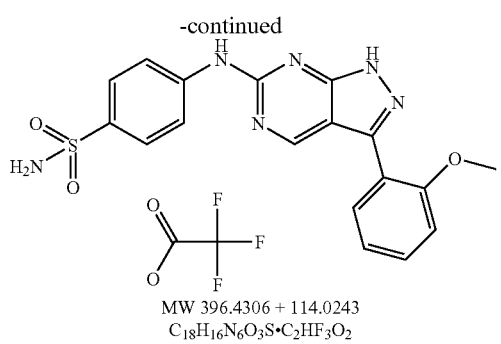

MW 396.4306 + 114.0243
C₁₈H₁₆N₆O₃S·C₂HF₃O₂

6-Chloro-3-(2-methoxy-phenyl)-1H-pyrazolo[3,4-d]pyrimidine (Example 6, 50 mg, 0.192 mmol) and sulfanilamide (Aldrich, 47.6 mg. 0.276 mmol, Aldrich) were combined with 2-propanol (1 ml) in a microwave tube and was heated at 170° C. for 10 minutes in a Microwave Oven (SmithSynthesizer, Personal Chemistry), cooled and the suspension was filtered and the solid collected and washed with cold 2-propanol. HPLC purification gave 40.1 mg (41%) as a TFA salt. MS (M+H)+, 397.1.

Example 33

[3-(2,6-Difluoro-phenyl)-1H-pyrazolo[3,4-d]pyrimidin-6-yl]-(4-fluoro-phenyl)-amine

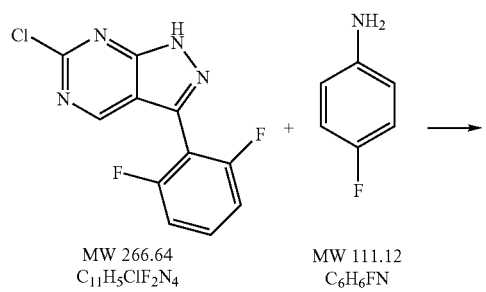

MW 266.64          MW 111.12
C₁₁H₅ClF₂N₄        C₆H₆FN

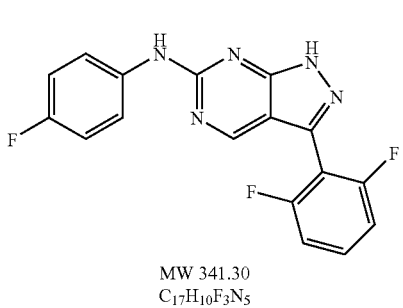

MW 341.30
C₁₇H₁₀F₃N₅

The compound was prepared from 6-chloro-3-(2,6-difluoro-phenyl)-1H-pyrazolo[3,4-d]pyrimidine (Example 12) and 4-fluoroaniline (Aldrich) in an analogous manner as described in Example 32 (160° C.). Filtration and washing with 2-propanol after the reaction gave the title product (59%). MS (M+H)+, 342.1

Example 34

2-[3-(2-Methoxy-phenyl)-1H-pyrazolo[3,4-d]pyrimidin-6-ylamino]-ethanol

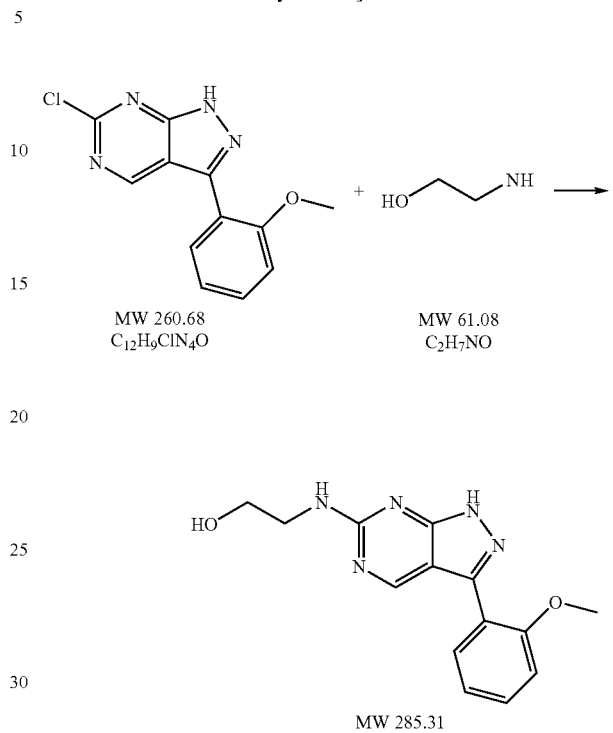

MW 260.68          MW 61.08
C₁₂H₉ClN₄O         C₂H₇NO

MW 285.31
C₁₄H₁₅N₅O₂

The compound was prepared from 6-chloro-3-(2-methoxy-phenyl)-1H-pyrazolo[3,4-d]pyrimidine (Example 6) and ethanoamine (AnaLaR) in an analogous manner as described in Example 32. HPLC purification gave the title compound (24 mg, 37% yield). MS (M+H)+, 286.2

Example 35

[3-(2-Methoxy-phenyl)-1H-pyrazolo[3,4-d]pyrimidin-6-yl]-pentane-1,5-diamine; compound with trifluoro-acetic acid MW 248.65
C₁₁H₆ClFN₄

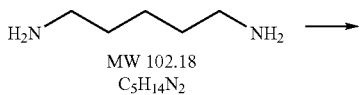

MW 102.18
C₅H₁₄N₂

-continued

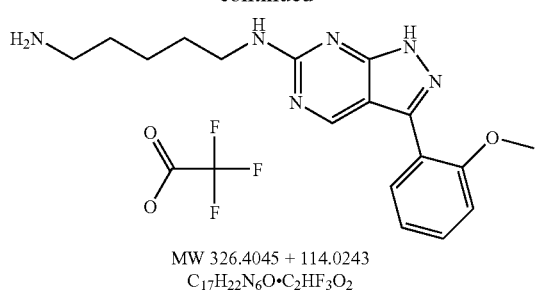

MW 326.4045 + 114.0243
C₁₇H₂₂N₆O•C₂HF₃O₂

The compound was prepared from 6-chloro-3-(2-methoxy-phenyl)-1H-pyrazolo[3,4-d]pyrimidine (Example 6) and 1,5-diaminopentane (ACROS) in an analogous manner as described in Example 32 (microwave at 120° C.). Purification with HPLC gave a TFA salt (68% yield). MS (M+H)+, 327.3.

Example 36

N'-[3-(2-Methoxy-phenyl)-1H-pyrazolo[3,4-d]pyrimidin-6-yl]-N,N-dimethyl-propane-1,3-diamine

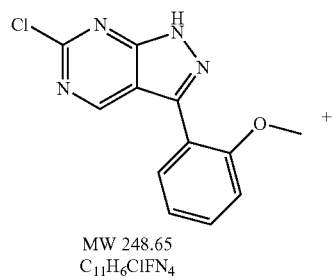

MW 248.65
C₁₁H₆ClFN₄

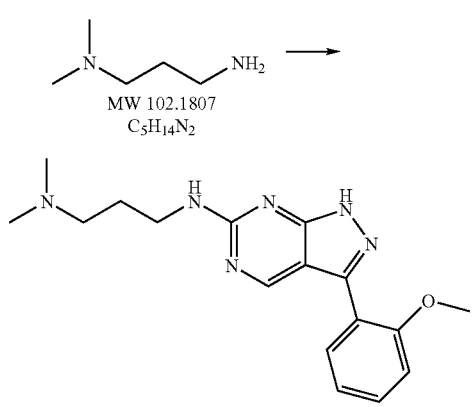

MW 326.40
C₁₇H₂₂N₆O

The compound was prepared from 6-chloro-3-(2-methoxy-phenyl)-1H-pyrazolo[3,4-d]pyrimidine (Example 6) and 3-dimethylamino propylamine (Aldrich) in an analogous manner as described in Example 32 (120° C.) and 9.2 mg (12% yield) free base was obtained. Purification of the mother liquor with HPLC gave a TFA salt (50 mg, 49% yield) MS (M+H)+, 327.2.

Example 37

N-[3-(2-Methoxy-phenyl)-1H-pyrazolo[3,4-d]pyrimidin-6-yl]-N,N-dimethyl-pentane-1,5-diamine; compound with trifluoro-acetic acid

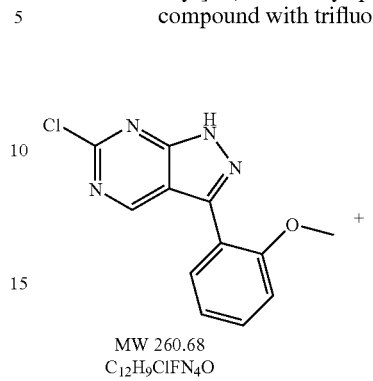

MW 260.68
C₁₂H₉ClFN₄O

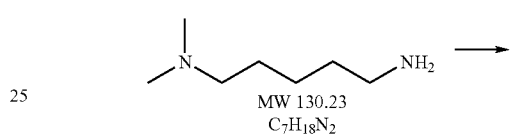

MW 130.23
C₇H₁₈N₂

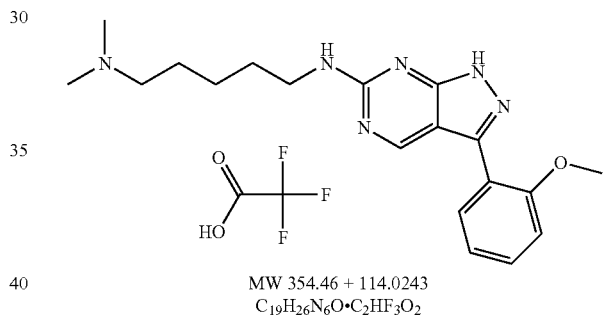

MW 354.46 + 114.0243
C₁₉H₂₆N₆O•C₂HF₃O₂

The compound was prepared from 6-chloro-3-(2-methoxy-phenyl)-1H-pyrazolo[3,4-d]pyrimidine (Example 6) and 5-(dimethylamino)amylamine (Matrix) in an analogous manner as described in Example 32(120° C.). Purification with HPLC gave a TFA salt (59% yield). MS (M+H)+, 355.25.

Example 38

[3-(2-Methoxy-phenyl)-1H-pyrazolo[3,4-d]pyrimidin-6-yl]-phenyl-amine

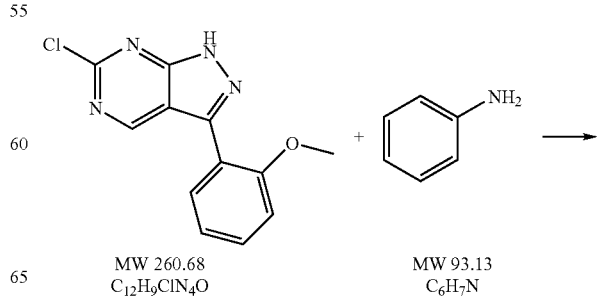

MW 260.68           MW 93.13
C₁₂H₉ClN₄O          C₆H₇N

-continued

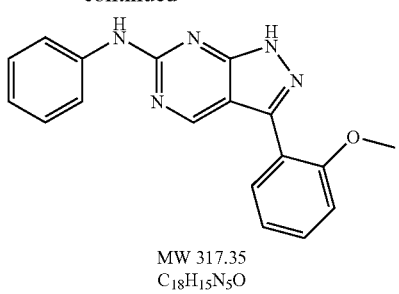

MW 317.35
C₁₈H₁₅N₅O

The compound was prepared from 6-chloro-3-(2-methoxy-phenyl)-1H-pyrazolo[3,4-d]pyrimidine (Example 6) and aniline (Aldrich) in an analogous manner as described in Example 32 (175° C.) and the title compound was obtained in 69% yield. MS (M+H)+, 318.2.

Example 39

(4-Methoxy-phenyl)-[3-(2-methoxy-phenyl)-1H-pyrazolo[3,4-d]pyrimidin-6-y]-amine; compound with trifluoro-acetic acid

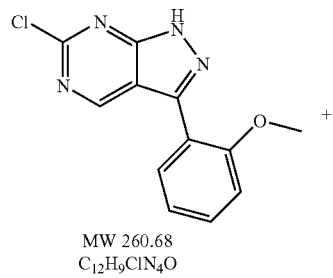

MW 260.68
C₁₂H₉ClN₄O

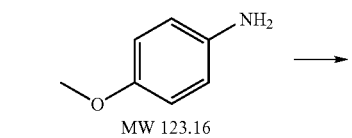

MW 123.16
C₆H₉NO

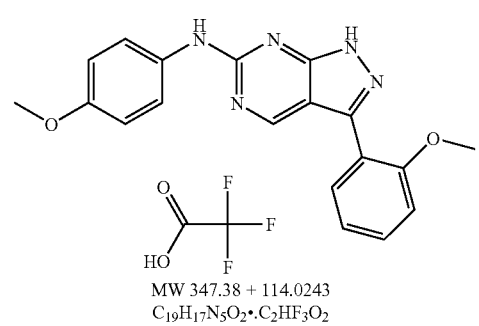

MW 347.38 + 114.0243
C₁₉H₁₇N₅O₂•C₂HF₃O₂

The compound was prepared from 6-chloro-3-(2-methoxy-phenyl)-1H-pyrazolo[3,4-d]pyrimidine (Example 6) and p-Anisidine (Aldrich) in an analogous manner as described in Example 32 (175° C.). Purification with HPLC gave the title compound as the TFA salt (48% yield). MS (M+H)+, 348.2.

Example 40

[3-(2,6-Difluoro-phenyl)-1H-pyrazolo[3,4-d]pyrimidin-6-yl]-(2-methoxy-phenyl)-amine; compound with trifluoro-acetic acid

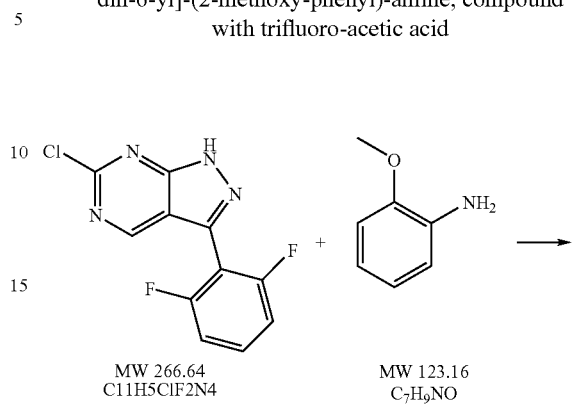

MW 266.64
C11H5ClF2N4

MW 123.16
C₇H₉NO

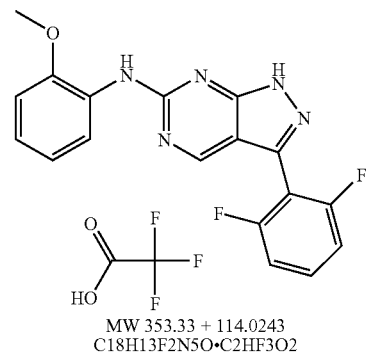

MW 353.33 + 114.0243
C18H13F2N5O•C2HF3O2

The compound was prepared from 6-chloro-3-(2,6-difluoro-phenyl)-1H-pyrazolo[3,4-d]pyrimidine (Example 12) and o-anisidine (Aldrich) in an analogous manner as described in Example 32 (160° C.). Purification with HPLC gave a TFA salt (42% yield). MS (M+H)+, 354.1.

Example 41

4-(3-Methyl-1H-pyrazolo[3,4-d]pyrimidin-6-ylamino)-benzenesulfonamide; compound with trifluoro-acetic acid

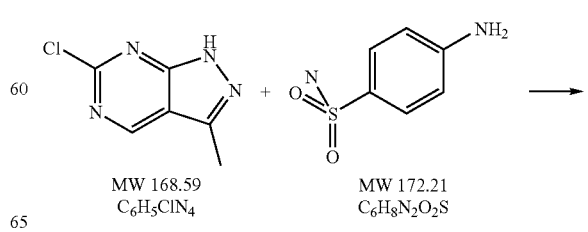

MW 168.59
C₆H₅ClN₄

MW 172.21
C₆H₈N₂O₂S

41

-continued

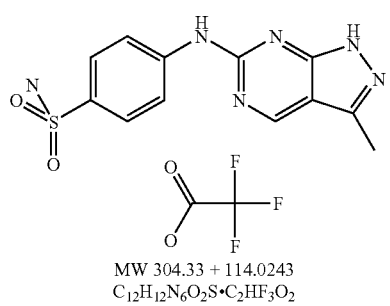

MW 304.33 + 114.0243
C₁₂H₁₂N₆O₂S•C₂HF₃O₂

The compound was prepared from 6-chloro-3-methyl-1H-pyrazolo[3,4-d]pyrimidine (Example 22) and sulfanilamide (Aldrich) in an analogous manner as described in Example 32 (175° C.). Purification with HPLC gave the title compound as a TFA salt (13%). MS (M+H)+, 305.0.

Example 42

2-(3-Methyl-1H-pyrazolo[3,4-d]pyrimidin-6-ylamino)-ethanol; compound with trifluoro-acetic acid

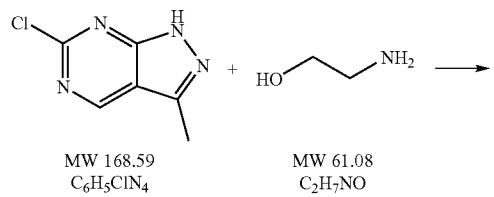

MW 168.59            MW 61.08
C₆H₅ClN₄             C₂H₇NO

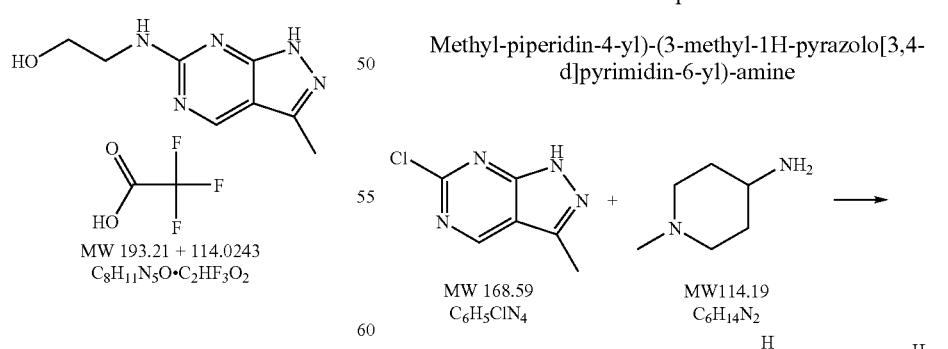

MW 193.21 + 114.0243
C₈H₁₁N₅O•C₂HF₃O₂

The compound was prepared from 6-chloro-3-methyl-1H-pyrazolo[3,4-d]pyrimidine (Example 22) and ethanoamine (AnaLaR) in an analogous manner as described in Example 32 (120° C.). Purification with HPLC gave a TFA salt in 56% yield. MS (M+H)+, 193.9.

42

Example 43

4-[3-(3-Fluoro-phenyl)-1H-pyrazolo[3,4-d]pyrimidin-6-ylamino]-piperidine-1-carboxylic acid ethyl ester; compound with trifluoro-acetic acid

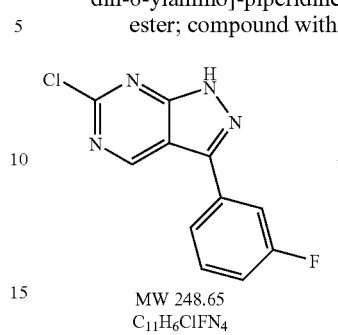

MW 248.65
C₁₁H₆ClFN₄

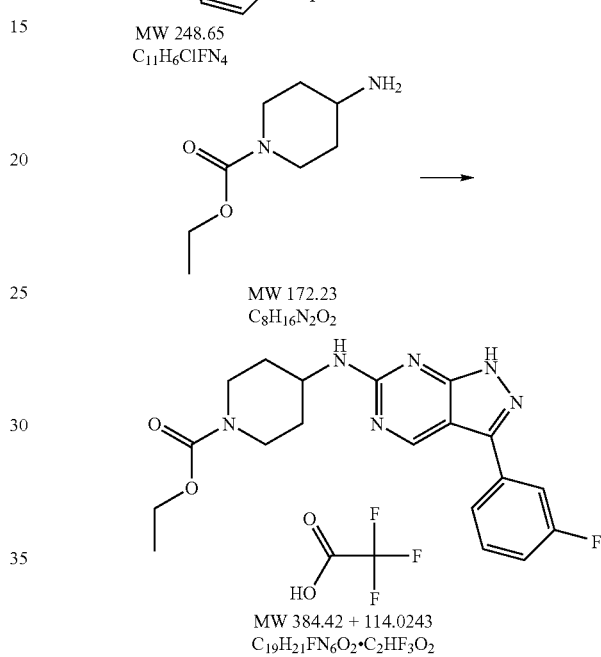

MW 172.23
C₈H₁₆N₂O₂

MW 384.42 + 114.0243
C₁₉H₂₁FN₆O₂•C₂HF₃O₂

The compound was prepared from 6-chloro-3-(3-fluorophenyl)-1H-pyrazolo[3,4-d]pyrimidine (Example 9) and ethyl 4-amino-1-piperidine carboxylate (Aldrich) in an analogous manner as described in Example 32 (160° C.). Purification with HPLC gave a TFA salt in 18% yield. MS (M+H)+, 385.1.

Example 44

Methyl-piperidin-4-yl)-(3-methyl-1H-pyrazolo[3,4-d]pyrimidin-6-yl)-amine

MW 168.59            MW114.19
C₆H₅ClN₄             C₆H₁₄N₂

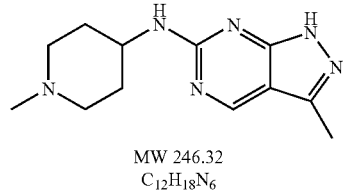

MW 246.32
C₁₂H₁₈N₆

The compound was prepared from 6-Chloro-3-methyl-1H-pyrazolo[3,4-d]pyrimidine (Example 22) and 4-amino-N-methylpiperidine (Aldrich) in an analogous manner as described in Example 32. MS (M+H)+, 247.

Example 45

The pharmacological properties of the compounds of this invention may be confirmed by a number of pharmacological assays. The exemplified pharmacological assays which follow have been carried out with the compounds according to the invention and their salts. The compounds of the invention exhibited Cdk4/cyclin D activity with IC50 values and Ki values of less than 1.0 μM. Additionally, the antiproliferative potency of some compounds of the invention was tested in the human colon tumor cell line HCT116 with IC90 values reported from an MTT assay of less than 30 μM, preferably less than 5 μM.

Kinase Assays

To determine inhibition of Cdk4, Cdk2 and Cdk1 activity, kinase assays were conducted using FlashPlate™ assays (NEN™-Life Science Products). FlashPlate assays were performed using recombinant human cyclin B-Cdk1, human cyclin E-Cdk2 or human cyclin D1-Cdk4 complexes. GST-cyclinE (GST-cycE), Cdk2, GST-cyclinB (GST-cycB), Cdk1, GST-Cdk4 and cyclin D1 (cycD1) cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805-816). A 6×-Histidine tagged truncated form of retinoblastoma (Rb) protein (amino acid 386-928) was used as the substrate for the cycD1-Cdk4, cycB-Cdk1 and the cycE-Cdk2 assays (the expression plasmid was provided by Dr. Veronica Sullivan, Department of Molecular Virology, Roche Research Centre, Welwyn Garden City, United Kingdom). The Rb protein is a natural substrate for phosphorylation by Cdk4, Cdk2 and Cdk1 (see Herwig and Strauss Eur. J. Biochem. Vol. 246 (1997) pp. 581-601 and the references cited therein).

The expression of the 62 Kd protein was under the control of an IPTG inducible promoter in an M15 E. coli strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For all three kinase assays reported herein, 96-well Flash-Plates were coated with Rb protein at 10 μg/ml, using 100 μl per well. Plates were incubated at 4° C. overnight or at room temperature for 3 hours on a shaker. To control for nonspecific phosphorylation, one row of wells was coated with 100 μl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 μl reaction mix (25 mM HEPES, 20 mM MgCl2, 0.002% Tween 20, 2 mM DTT, 1 μM ATP, 4 nM 33P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of Cdk activity, was determined according to the following formula:

$$100 \times 1 - \frac{\text{test compound} - \text{nonspecific}}{\text{total} - \text{nonspecific}}$$

where "test compound" refers to the average counts per minute of the test duplicates, "nonspecific" refers to the average counts per minute when no CyclinD/Cdk4, etc., was added, and "total" refers to the average counts per minute when no compound was added. The IC50 value is the concentration of test compound that reduces by 50% the protein-kinase induced incorporation of the radiolabel under the test conditions described.

The results of the foregoing in vitro experiments are set forth in Table 1 below. The IC50 values are summarized in the Table 1 below.

Cell Based Assays (Tetrazolium Dye Proliferation Assay)

Proliferation was evaluated by the tetrazolium dye assay according to the procedure of Denizot and Lang (Denizot, F. and Lang, R. J Immunol Methods 1986, 89, 271-277). The cell line used was HCT116, a colorectal carcinoma cell line obtained from the American Type Cell Culture Collection (ATCC; Rockville, Md.). The cells were grown in McCoy's 5A medium supplemented with 10% FCS and L-glutamine.

Cells were plated at the appropriate seeding density to give logarithmic growth over the course of the assay in a 96-well tissue culture plate. Plates were incubated overnight at 37° C. in a humidified incubator with 5% CO2. The next day, test compounds were serially diluted to four times the final concentration in the appropriate medium containing 1.2% DMSO. One-fourth final volume of each dilution was added in duplicate to the plates containing cells. The same volume of 1.2% DMSO in medium was added to a row of "control wells" such that the final concentration of DMSO in each well was 0.3%. Wells to which no cells were added served as the "blank." Wells to which no inhibitor was added served as "no inhibitor control." The plates were) returned to the incubator, and at set time points (determined by their growth curves) plates were analyzed as described below.

3-(4,5-dimethylthiazole-2-yl)-2,5-diphenyl-2H-tetrazolium bromide (thiazolyl blue; MTT; Sigma) was added to each well to yield a final concentration of 1 mg/ml. Plates were returned to the incubator for 2.5-3 hours at 37° C. The MTT-containing medium was removed and the resulting formazan metabolite was solubilized in 100% ethanol with shaking for 15 minutes at room temperature. Absorbance readings were taken in a microtiter plate reader (Dynatech and Molecular Devices plate readers were used interchangeably) at a wavelength of 570 nm with a 650 nm reference. Percent inhibition (% INH) is calculated by subtracting the absorbance of the blank well from all wells, then subtracting the ratio of the average absorbance of each test duplicate (SAVE) by the average of the controls (CAVE) from 1.00. The final number is then multiplied by 100 (% INH=(1.00−SAVE/CAVE)×100). The concentration at which 50% inhibition of cell proliferation is obtained (the IC50) is determined from the linear regression of a plot of the logarithm of the concentration versus percent inhibition. The IC50 values are also shown in Table 1 below.

TABLE 1

This table shows the $IC_{50}$s of compounds of the instant Examples in Cdk4, Cdk2, and $Cdk_1$ kinase assays, and also the $IC_{50}$s in the cell-based assays ("MTT") assay.

| Example Number | Cdk4 $IC_{50}(\mu M)$ | Cdk2 $IC_{50}(\mu M)$ | Cdk1 $IC_{50}(\mu M)$ | MTT $IC_{50}(\mu M)$ |
|---|---|---|---|---|
| Example 16 | 0.041 | 0.244 | nd | 4.5 |
| Example 19 | 0.278 | 0.033 | 0.231 | 9.16 |
| Example 23 | 0.278 | 0.278 | 1.46 | nd |
| Example 25 | 0.042 | 0.077 | nd | nd |
| Example 26 | 0.199 | 0.114 | nd | nd |
| Example 27 | 0.004 | 0.275 | nd | 1.7 |
| Example 28 | 0.014 | 0.018 | 0.107 | 1.2 |
| Example 29 | 0.278 | 0.278 | 0.867 | 32 |
| Example 30 | 0.128 | 0.179 | 0.262 | 3.93 |
| Example 31 | 0.0185 | 0.23 | 1.136 | 30 |
| Example 32 | 0.036 | 0.009 | nd | nd |
| Example 33 | 2.5 | 2.5 | nd | nd |
| Example 34 | 0.344 | 0.594 | nd | nd |
| Example 35 | 1.119 | 1.852 | nd | nd |
| Example 36 | 0.278 | 0.278 | nd | nd |
| Example 37 | 0.278 | 0.278 | nd | nd |
| Example 38 | 0.278 | 0.278 | nd | nd |
| Example 39 | 0.278 | 0.278 | nd | nd |
| Example 40 | 0.278 | 0.278 | nd | nd |
| Example 41 | 0.278 | 0.024 | nd | nd |
| Example 42 | 0.278 | 0.278 | nd | nd |
| Example 43 | 0.278 | 0.278 | nd | nd |
| Example 44 | 0.278 | 0.278 | nd | nd |

Nd means "not determined".

Example 46

Tablet Formulation

| Item | Ingredients | Mg/Tablet | | | | | |
|---|---|---|---|---|---|---|---|
| 1 | Compound A * | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

* Compound A represents a compound of the invention.

Manufacturing Procedure:

Mix Items 1, 2 and 3 in a suitable mixer for 15 minutes.

Granulate the powder mix from Step 1 with 20% Povidone K30 Solution (Item 4).

Dry the granulation from Step 2 at 50° C.

Pass the granulation from Step 3 through a suitable milling equipment.

Add the Item 5 to the milled granulation Step 4 and mix for 3 minutes.

Compress the granulation from Step 5 on a suitable press.

Example 47

Capsule Formulation

| Item | Ingredients | mg/Capsule | | | | |
|---|---|---|---|---|---|---|
| 1 | Compound A * | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

* Compound A represents a compound of the invention.

Manufacturing Procedure:

Mix Items 1, 2 and 3 in a suitable mixer for 15 minutes.

Add Items 4 & 5 and mix for 3 minutes.

Fill into a suitable capsule.

Example 48

Injection Solution/Emulsion Preparation

| Item | Ingredient | mg/mL |
|---|---|---|
| 1 | Compound A * | 1 mg |
| 2 | PEG 400 | 10-50 mg |
| 3 | Lecithin | 20-50 mg |
| 4 | Soy Oil | 1-5 mg |
| 5 | Glycerol | 8-12 mg |
| 6 | Water q.s. | 1 mL |

* Compound A represents a compound of the invention.

Manufacturing Procedure:

Dissolve item 1 in item 2.

Add items 3, 4 and 5 to item 6 and mix until dispersed, then homogenize.

Add the solution from step 1 to the mixture from step 2 and homogenize until the dispersion is translucent.

Sterile filter through a 0.2 μm filter and fill into vials.

Example 49

Injection Solution/Emulsion Preparation

| Item | Ingredient | mg/mL |
|---|---|---|
| 1 | Compound A * | 1 mg |
| 2 | Glycofurol | 10-50 mg |
| 3 | Lecithin | 20-50 mg |
| 4 | Soy Oil | 1-5 mg |
| 5 | Glycerol | 8-12 mg |
| 6 | Water | q.s. 1 mL |

* Compound A represents a compound of the invention.

Manufacturing Procedure:

Dissolve item 1 in item 2.

Add items 3, 4 and 5 to item 6 and mix until dispersed, then homogenize.

As the solution from step 1 to the mixture from step 2 and homogenize until the dispersion is translucent.

Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:

1. A compound of formula (I)

$$\text{(I)}$$

or a pharmaceutically acceptable salt thereof, wherein
$R^1$ is selected from the group consisting of:
(a) piperidine, piperazine or pyrrolidine which may be substituted by up to four substituents independently selected from the group consisting of:
(i) lower alkyl which may be substituted by OH, $CO_2R^3$, $COR^4$, $CONR^5R^6$, $NR^5R^6$, $OR^7$, or $S(O)nR^8$; and
(ii) $CO_2R^3$, $COR^4$, $CONR^5R^6$, $NR^5R^6$, $OR^7$, or $S(O)nR^8$;
(b) phenyl, tolyl or xylyl which is substituted by up to four substituents independently selected from the group consisting of:
$SO_2CH_3$, $SO_2NH_2$, $NH_2$, $N(CH_3)_2$, OH, $OCH_3$ or $COOCH_2CH_3$; and
(c) cyclopropyl, cyclobutyl, cyclopentyl or cyclohexyl that is substituted by $OR^7$, $NR^5R^6$, or $S(O)nR^8$;
$R^2$ is phenyl which may be substituted with fluorine and methoxy;
$R^3$ is selected from the group consisting of:
(i) lower alkyl which may be substituted by $OR^7$, $COR^4$, $NR^5R^6$ or $CONR^5R^6$; and
(ii) cycloalkyl which may be substituted by OH or $NH_2$;
$R^4$ is selected from the group consisting of:
(i) H; and
(ii) lower alkyl which may be substituted by $OR^7$ or $NR^5R^6$;
$R^5$ and $R^6$ are each independently selected from the group consisting of:
(i) H;
(ii) lower alkyl which may be substituted by OH, $CO_2R^3$, $CONR^{10}R^{11}$, $SO_2R^3$, $OR^7$, $NR^{10}R^{11}$, heterocycle, or heteroaryl;
(iii) cycloalkyl which may be substituted by $CO_2R^3$, $CONR^{10}R^{11}$, $SO_2R^4$, $OR^7$, or $NR^{10}R^{11}$;
(iv) aryl which may be substituted by $CO_2R^3$, $CONR^{10}R^{11}$, $SO_2R^3$, $OR^7$, $NR^{10}R^{11}$, halogen, lower alkyl, and lower alkyl substituted by halogen, $CO_2R3$, $CONR^{10}R^{11}$, $OR^7$, $NR^{10}R^{11}$, or OH;
(v) $SO_2R^3$;
(vi) $CO_2R^3$, and
(vii) $COR^3$; or
alternatively, $NR^5R^6$ can form a ring having a total of 3-7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $NR^5R^6$, lower alkyl, and lower alkyl substituted by $OR^7$;
$R^7$ is selected from the group consisting of H and lower alkyl optionally substituted by $NR^5R^6$ or $OR^9$;
$R^8$ is selected from the group consisting of:
(i) aryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, and OH;
(ii) heteroaryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, or OH;
(iii) $NR^5R^6$;
(iv) lower alkyl which may be substituted by halogen, $CO_2R^3$, $CONR^5R^6$, $OR^7$, $NR^5R^6$, or OH; and
(v) heterocycle which may be substituted by $CO_2R^3$, $COR^3$, $SO_2R^3$, $CONR^5R^6$, $OR^7$, or $NR^5R^6$;
$R^9$ is selected from the group consisting of H, lower alkyl, and lower alkyl substituted by OH or halogen;
$R^{10}$ and $R^{11}$ are each independently selected from the group consisting of:
(i) H;
(ii) lower alkyl which may be substituted by OH, $CO_2R^3$, $CONR^5R^6$, $SO_2R^3$, $OR^7$, $NR^5R^6$, heterocycle, or heteroaryl;
(iii) cycloalkyl which may be substituted by $CO_2R^3$, $CONR^5R^6$, $SO_2R^3$, $OR^7$, or $NR^5R^6$;
(iv) aryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, or OH;
(v) $SO_2R^3$;
(vi) $CO_2R^3$ and
(vii) $COR^3$; or
alternatively, $NR^{10}R^{11}$ can form a ring having a total of 3-7 ring atoms, said ring atoms comprising in addition to the nitrogen to which $R^{10}$ and $R^{11}$ are bonded, carbon ring atoms, said carbon ring atoms optionally being replaced by one or more additional N or O ring atoms or the group $SO_2$, and said ring atoms optionally being substituted by OH, oxo, $NR^5R^6$, lower alkyl and lower alkyl substituted by $OR^7$ and n is 1 or 2.

2. The compound of claim 1, wherein $R^1$ is selected from the group consisting of piperidine and phenyl.

3. The compound of claim 2, wherein $R^1$ is substituted by $SO_2CH_3$, $CH_3$, $COOCH_2CH_3$, $SO_2NH_2$, F, $OCH_3$, OH, $NH_2$, or $N(CH_3)_2$.

4. The compound of claim 1, wherein $R^2$ is phenyl.

5. The compound of claim 1, wherein $R^2$ is phenyl that is substituted with methoxy at the 2 position on the ring.

6. A compound selected from the group consisting of
[3-(2,3-Difluoro-6-methoxy-phenyl)-1H-pyrazolo[3,4-d] pyrimidin-6-yl]-(1-methanesulfonyl-piperidin-4-yl)-amine
(1-Methanesulfonyl-piperidin-4-yl)-(1H-pyrazolo[3,4-d] pyrimidin-6-yl)-amine
(1-Methyl-piperidin-4-yl)-(3-methyl-1H-pyrazolo[3,4-d] pyrimidin-6-yl)-amine
[3-(5-Fluoro-2-methoxy-phenyl)-1H-pyrazolo[3,4-d]pyrimidin-6-yl]-(1-methanesulfonyl-piperidin-4-yl)-amine
[3-(5-Fluoro-2-methoxy-phenyl)-1H-pyrazolo[3,4-d]pyrimidin-6-yl]-(1-methanesulfonyl-piperidin-4-yl)-amine

[3-(5-Fluoro-2-methoxy-phenyl)-1H-pyrazolo[3,4-d]pyrimidin-6-yl]-(1-methanesulfonyl-piperidin-4-yl)-amine
(1-Methanesulfonyl-piperidin-4-yl)-[3-(2-methoxy-phenyl)-1H-pyrazolo[3,4-d]pyrimidin-6-yl]-amine; compound with trifluoro-acetic acid
[3-(2,6-Difluoro-phenyl)-1H-pyrazolo[3,4-d]pyrimidin-6-yl]-(1-methanesulfonyl-piperidin-4-yl)-amine
(1-Methanesulfonyl-piperidin-4-yl)-(3-phenyl-1H-pyrazolo[3,4-d]pyrimidin-6-yl)-amine, and
[3-(3-Fluoro-phenyl)-1H-pyrazolo[3,4-d]pyrimidin-6-yl]-(1-methanesulfonyl-piperidin-4-yl)-amine.

7. A compound selected from the group consisting of
4-[3-(2-Methoxy-phenyl)-1H-pyrazolo[3,4-d]pyrimidin-6-ylamino]-benzenesulfonamide; compound with trifluoro-acetic acid
[3-(2,6-Difluoro-phenyl)-1H-pyrazolo[3,4-d]pyrimidin-6-yl]-(4-fluoro-phenyl)-amine
2-[3-(2-Methoxy-phenyl)-1H-pyrazolo[3,4-d]pyrimidin-6-ylamino]-ethanol
[3-(2-Methoxy-phenyl)-1H-pyrazolo[3,4-d]pyrimidin-6-yl]-pentane-1,5-diamine; compound with trifluoro-acetic acid
N'-[3-(2-Methoxy-phenyl)-1H-pyrazolo[3,4-d]pyrimidin-6-yl]-N,N-dimethyl-propane-1,3-diamine
N-[3-(2-Methoxy-phenyl)-1H-pyrazolo[3,4-d]pyrimidin-6-yl]-N,N-dimethyl-pentane-1,5-diamine; compound with trifluoro-acetic acid
(4-Methoxy-phenyl)-[3-(2-methoxy-phenyl)-1H-pyrazolo[3,4-d]pyrimidin-6-yl]-amine; compound with trifluoro-acetic acid
[3-(2,6-Difluoro-phenyl)-1H-pyrazolo[3,4-d]pyrimidin-6-yl]-(2-methoxy-phenyl)-amine; compound with trifluoro-acetic acid
4-(3-Methyl-1H-pyrazolo[3,4-d]pyrimidin-6-ylamino)-benzenesulfonamide; compound with trifluoro-acetic acid
2-(3-Methyl-1H-pyrazolo[3,4-d]pyrimidin-6-ylamino)-ethanol; compound with trifluoro-acetic acid
4-[3-(3-flouro-phenyl)-1H-pyrazolo[3,4-d]pyrimidin-6-ylamino]-piperidine-1-carboxylic acid ethyl ester; compound with triflouro-acetic acid, and
(1-Methyl-piperidin-4-yl)-(3-methyl-1H-pyrazolo[3,4-d]pyrimidin-6-yl)-amine.

8. A compound selected from the group consisting of
[3-(2,3-Difluoro-6-methoxy-phenyl)-1H-pyrazolo[3,4-d]pyrimidin-6-yl]-(1-methanesulfonyl-piperidin-4-yl)-amine
(1-Methanesulfonyl-piperidin-4-yl)-(1H-pyrazolo[3,4-d]pyrimidin-6-yl)-amine,
[3-(5-Fluoro-2-methoxy-phenyl)-1H-pyrazolo[3,4-d]pyrimidin-6-yl]-(1-methanesulfonyl-piperidin-4-yl)-amine,
[3-(5-Fluoro-2-methoxy-phenyl)-1H-pyrazolo[3,4-d]pyrimidin-6-yl]-(1-methanesulfonyl-piperidin-4-yl)-amine,
(1-Methanesulfonyl-piperidin-4-yl)-[3-(2-methoxy-phenyl)-1H-pyrazolo[3,4-d]pyrimidin-6-yl]-amine; compound with trifluoro-acetic acid,
[3-(3-Fluoro-phenyl)-1H-pyrazolo[3,4-d]pyrimidin-6-yl]-(1-methanesulfonyl-piperidin-4-yl)-amine, and
4-[3-(2-Methoxy-phenyl)-1H-pyrazolo[3,4-d]pyrimidin-6-ylamino]-benzenesulfonamide; compound with trifluoro-acetic acid.

9. A pharmaceutical formulation which comprises a compound of formula (I)

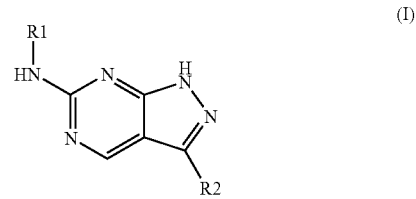

or a pharmaceutically acceptable salt thereof, wherein
$R^1$ is selected from the group consisting of:
(a) piperidine, piperazine or pyrrolidine which may be substituted by up to four substituents independently selected from the group consisting of:
(i) lower alkyl which may be substituted by OH, $CO_2R^3$, $COR^4$, $CONR^5R^6$, $NR^5R^6$, $OR^7$, or $S(O)nR^8$; and
(ii) $CO_2R^3$, $COR^4$, $CONR^5R^6$, $NR^5R^6$, $OR^7$, or $S(O)nR^8$;
(b) phenyl, tolyl or xylyl that is substituted by up to four substituents independently selected from the group consisting of:
(i) $SO_2CH_3$, $SO_2NH_2$, $NH_2$, $N(CH_3)_2$, OH, $OCH_3$ or $COOCH_2CH_3$; and
(c) cyclopentyl, cyclobutyl, cyclopentyl or cyclohexyl that is substituted by $OR^7$, $NR^5R^6$, or $S(O)nR^8$;
$R^2$ is
phenyl which may be substituted with fluorine and methoxy;
$R^3$ is selected from the group consisting of:
(i) lower alkyl which may be substituted by $OR^7$, $COR^4$, $NR^5R^6$ or $CONR^5R^6$; and
(ii) cycloalkyl which may be substituted by OH or $NH_2$;
$R^4$ is selected from the group consisting of:
(i) H; and
(ii) lower alkyl which may be substituted by $OR^7$ or $NR^5R^6$;
$R^5$ and $R^6$ are each independently selected from the group consisting of:
(i) H;
(ii) lower alkyl which may be substituted by OH, $CO_2R^3$, $CONR^{10}R^{11}$, $SO_2R^3$, $OR^7$, $NR^{10}R^{11}$, heterocycle, or heteroaryl;
(iii) cycloalkyl which may be substituted by $CO_2R^3$, $CONR^{10}R^{11}$, $SO_2R^4$, $OR^7$, or $NR^{10}R^{11}$;
(iv) aryl which may be substituted by $CO_2R^3$, $CONR^{10}R^{11}$, $SO_2R^3$, $OR^7$, $NR^{10}R^{11}$, halogen, lower alkyl, and lower alkyl substituted by halogen, CO2R3, $CONR^{10}R^{11}$, $OR^7$, $NR^{10}R^{11}$, or OH;
(v) $SO_2R^3$;
(vi) $CO_2R^3$, and
(vii) $COR^3$; or
alternatively, $NR^5R^6$ can form a ring having a total of 3-7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $NR^5R^6$, lower alkyl, and lower alkyl substituted by $OR^7$;

$R^7$ is selected from the group consisting of H and lower alkyl optionally substituted by $NR^5R^6$ or $OR^9$;

$R^8$ is selected from the group consisting of:
  (i) aryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, and OH;
  (ii) heteroaryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, or OH;
  (iii) $NR^5R^6$;
  (iv) lower alkyl which may be substituted by halogen, $CO_2R^3$, $CONR^5R^6$, $OR^7$, $NR^5R^6$, or OH; and
  (v) heterocycle which may be substituted by $CO_2R^3$, $COR^3$, $SO_2R^3$, $CONR^5R^6$, $OR^7$, or $NR^5R^6$;

$R^9$ is selected from the group consisting of H, lower alkyl, and lower alkyl substituted by OH or halogen;

$R^{10}$ and $R^{11}$ are each independently selected from the group consisting of:
  (i) H;
  (ii) lower alkyl which may be substituted by OH, $CO_2R^3$, $CONR^5R^6$, $SO_2R^3$, $OR^7$, $NR^5R^6$, heterocycle, or heteroaryl;
  (iii) cycloalkyl which may be substituted by $CO_2R^3$, $CONR^5R^6$, $SO_2R^3$, $OR^7$, or $NR^5R^6$;
  (iv) aryl which may be substituted by $CO_2R^3$, $CONR^5R^6$, $SO_2R^3$, $OR^7$, $NR^5R^6$, halogen, lower alkyl, or lower alkyl substituted by halogen, $CO_2R^3$, $CONR^5R^6$, $OR^7$, $NR^5R^6$, or OH;
  (v) $SO_2R^3$;
  (vi) $CO_2R^3$ and
  (vii) $COR^3$; or alternatively, $NR^{10}R^{11}$ can form a ring having a total of 3-7 ring atoms, said ring atoms comprising in addition to the nitrogen to which $R^{10}$ and $R^{11}$ are bonded, carbon ring atoms, said carbon ring atoms optionally being replaced by one or more additional N or O ring atoms or the group $SO_2$, and said ring atoms optionally being substituted by OH, oxo, $NR^5R^6$, lower alkyl and lower alkyl substituted by $OR^7$ and n is 1 or 2 and a pharmaceutically acceptable excipient.

10. The compound [3-(2-Methoxy-phenyl)-1H-pyrazolo[3,4-d]pyrimidin-6-yl]-phenyl-amine.

11. The compound of claim 5 wherein $R^2$ is further substituted with fluorine.

12. The compound of claim 2 wherein $R^1$ is phenyl that is substituted by $SO_2NH_2$ or methoxy and $R^2$ is phenyl substituted by methoxy and/or fluorine.

13. The compound of claim 12 which is 4-[3-(2-Methoxy-phenyl)-1H-pyrazolo[3,4-d]pyrimidin-6-ylamino]-benzenesulfonamide.

* * * * *

UNITED STATES PATENT AND TRADEMARK OFFICE
CERTIFICATE OF CORRECTION

PATENT NO. : 7,405,220 B2
APPLICATION NO. : 11/136023
DATED : July 29, 2008
INVENTOR(S) : Ding et al.

It is certified that error appears in the above-identified patent and that said Letters Patent is hereby corrected as shown below:

ON TITLE PAGE:

Item (63) should read,
    The related U. S. application data reads "Provisional application No. 60/578,235, filed on Jun. 9, 2004". The related U. S. application data should read -- Provisional application No. 60/578,253, filed on Jun. 9, 2004 --.

Signed and Sealed this

Twenty-third Day of September, 2008

JON W. DUDAS
*Director of the United States Patent and Trademark Office*